(12) United States Patent
Hansen et al.

(10) Patent No.: US 10,131,899 B2
(45) Date of Patent: Nov. 20, 2018

(54) BIOACTIVE COMPOSITIONS FOR HIGH AVIDITY CELL CAPTURE

(71) Applicant: UT-Battelle, LLC, Oak Ridge, TN (US)

(72) Inventors: Ryan Robert Hansen, Knoxville, TN (US); Scott T. Retterer, Knoxville, TN (US); Bradley Steward Lokitz, Knoxville, TN (US); Jennifer L. Morrell-Falvey, Knoxville, TN (US); Juan Pablo Hinestrosa Salazar, San Diego, CA (US); Jamie Michael Messman, Leawood, KS (US); Sidney Michael Kilbey, II, Knoxville, TN (US); John Francis Ankner, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 26 days.

(21) Appl. No.: 14/215,552

(22) Filed: Mar. 17, 2014

(65) Prior Publication Data

US 2015/0259668 A1   Sep. 17, 2015

(51) Int. Cl.
| | | |
|---|---|---|
| C12N 11/08 | (2006.01) | |
| C12N 11/06 | (2006.01) | |
| C08F 293/00 | (2006.01) | |
| G03F 7/00 | (2006.01) | |

(52) U.S. Cl.
CPC ............ *C12N 11/08* (2013.01); *C08F 293/00* (2013.01); *C12N 11/06* (2013.01); *G03F 7/0002* (2013.01)

(58) Field of Classification Search
CPC ....... C12N 11/08; C12N 11/06; C08F 293/00; G03F 7/002
See application file for complete search history.

(56) References Cited

U.S. PATENT DOCUMENTS

| | | | |
|---|---|---|---|
| 3,922,203 A | 11/1975 | Aldridge, Jr. et al. | |
| 4,871,824 A * | 10/1989 | Heilmann ........ | A61K 39/39525 435/180 |
| 5,139,031 A | 8/1992 | Guirguis | |
| 5,200,471 A * | 4/1993 | Coleman .................. | C07K 1/22 424/78.08 |
| 7,923,241 B2 * | 4/2011 | Fang ...................... | C12M 25/06 435/287.9 |

OTHER PUBLICATIONS

Idota et al. "Novel temperature-responsive polymer brushes with carbohydrate residues facilitate selective adhesion and collection of hepatocytes." (2012) Science and Technology of Advanced Materials, vol. 13:1-9.*
Chen et al. "3-D Fabrication Technology for Tissue Engineering." (2007), BioMEMS and Biomedical Nanotechnolgy, vol. III: Therapeutic Micro/Nanotechnology: 29-38.*
Bandari et al. "Ring-opening metathesis polymerization-derived, lectin-functionalized monolithic supports for affinity separation of glycoproteins" (2013), Journal of Separation Science, vol. 36: 1169-1175.*
Fournier et al. "Well-defined Azlactone-Functionalized (Co)polymers on a Solid Support: Synthesis via Supported Living Radical Polymerization and Application as Nucleophile Scavengers" (2006) Journal of Combinatorial Chemistry, vol. 8: 522-530.*
Zhang et al. "Hierarchically imprinted poymer substrates for enhanced attachment of *Escherichia coli*" (2010) Journal of Colloid and Interface Science, vol. 343: 109-114.*
Pasparakis et al. "Synthetic polymers for capture and detection of microorganisms" (2007), Analyst: vol. 132: 1075-1082. (Year: 2007).*
Liu et al. "Fabricating three-dimensional carbohydrate hydrogel microarray for lectin-mediated bacterium capturing" (Mar. 2, 2014), Biosensors and Bioelectronics: vol. 58: 92-100. (Year: 2014).*
Buck M.E. et al., "Azlactone-Functionalized Polymers as Reactive Platforms for the Design of Advanced Materials Progress in the Last Ten Years", Polym. Chem. 3:66-80 (2012).
Buck M.E. et al., "Layer-by-Layer Fabrication of Covalently Cross-linked and Reactive Polymer Multilayers Using Azlactone-Functionalized Copolymers: A Platform for the Design of Functional Biointerfaces", Advanced Engineering Materials 13(10):B343-B352 (2011).
Buck M.E. et al., "Chemical Modification of Reactive Multilayered Films Fabricated from Poly(2-Alkenyl Azlactone)s: Design of Surfaces that Prevent or Promote Mammalian Cell Adhesion and Bacterial Biofilm Growth", Biomacromolecules 10(6):1564-1574 (2009).
Diaz C. et al., "Submicron Trenches Reduce the Pseudomonas Fluorescens Colonization Rate on Solid Surfaces", ACS Applied Materials & Interfaces 1(1):136-143 (2009).
Diaz C. et al., "Nano/Microscale Order Affects the Early Stages of Biofilm Formation on Metal Surfaces", Langmuir (2007) 23:11206-11210.
Hansen R.R. et al., "Microstructured Block Copolymer Surfaces for Control of Microbe Adhesion and Aggregation", Biosensors 4:63-75 (2014).

(Continued)

*Primary Examiner* — Teresa E Knight
(74) *Attorney, Agent, or Firm* — Scully Scott Murphy & Presser

(57) ABSTRACT

A composition useful for cell capture, the composition comprising a solid substrate on which is affixed a patterned polymer, and a cell-targeting agent attached to said patterned polymer, wherein said cell-targeting agent is exposed. Also described is a method for the preparation of the cell capturing composition, as well as flow through devices in which the cell capturing composition is incorporated. Further described is a method of capturing cells by contacting the cell-capturing composition with a liquid or gaseous sample containing cells. The method for capturing cells may also be a method for testing for the presence of one or more classes or species of cells or cellular organisms in a liquid or gaseous sample.

19 Claims, 13 Drawing Sheets

(56) References Cited

OTHER PUBLICATIONS

Hansen R.R. et al., "Lectin-Functionalized Poly(Glycidyl Methacrylate)-Block-Poly(Vinyldinnethyl Azlactone) Surface Scaffolds for High Aviditiy Microbial Capture", Biomacromolecules 14:3742-3748 (2013).
Hansen R., "Surface-Engineered Substrates for Functional Insights into Mammalian and Microbial Systems", NanoBio Conference, Oak Ridge National Laboratory, Oak Ridge, TN (May 24, 2013).
Lokitz B.S., "Surface Confinement of PGMA-b-PVDMA, a Dually Reactive Block Copolymer", 2013 Nano/Bio Sciences Workshop, Oak Ridge National Laboratory (Macromolecular Nanomaterials Group), Oak Ridge, TN (May 24, 2013).
Lokitz B.S. et al., "Manipulating Interfaces Through Surface Confinement of Poly(Glycidyl Methacrylate)-Block-Poly(Vinyldimethylazlactone), a Dually Reactive Block Copolymer", Macromolecules 45:6438-6449 (2012).
Rusmini F. et al., "Protein Immobilization Strategies for Protein Biochips", Biomacromolecules 8(6):1775-1789 (2007).
Walker B.N. et al., "Tailored Silicon Nanopost Arrays for Resonant Nanophotonic Ion Production", J. Phys. Chem. 114:4835-4840 (2010).
Yu Q. et al., "Nanopatterned Smart Polymer Surfaces for Controlled Attachment, Killing, and Release of Bacteria", ACS Applied Materials & Interfaces 5:9295-9304 (2013).
Zhao K. et al., "Psl Trails Guide Exploration and Microcolony Formation in Pseudomonas Aeruginosa Biofilms", Nature 479:388-391 (May 16, 2013).

* cited by examiner

BIOACTIVE COMPOSITIONS FOR HIGH AVIDITY CELL CAPTURE

This invention was made with government support under Prime Contract No. DE-AC05-00OR22725 awarded by the U.S. Department of Energy. The government has certain rights in the invention.

FIELD OF THE INVENTION

The present invention relates to compositions and methods for cell capture, and more particularly, the use of cell-targeting agents on a solid support for this purpose.

BACKGROUND OF THE INVENTION

The capture and study of microbes, either in liquid or air, remains an important field of study. Such methods permit a better understanding of the classes and phenotypes of microbes inhabiting a medium and further elucidation of mechanisms involved in their growth and proliferation. Unfortunately, a cost-effective method for cell capture and identification of specific types of microbes has remained elusive.

Cell surface carbohydrates, in particular, play an important role in a variety of processes related to cell growth and proliferation. In microbial systems, extracellular carbohydrates are critical in biofouling, host-microbe interactions, cell motility, and immune recognition processes. Due to the highly dynamic nature of extracellular glycan expression, an understanding of the role of exopolysaccharides (EPS) in many microbial systems is generally lacking. Currently, chromatography, mass spectroscopy and nuclear magnetic resonance (NMR) are among the techniques employed to analyze extracellular glycans, but these typically require additional processing steps that are likely to change the extracellular glycan concentration. This, in turn, generally make these analytical methods inaccurate, slow, low throughput, and expensive. Thus, there would be a significant benefit in a method of capture that could also be used to further elucidate the compositional and/or functional characteristics of cell surface carbohydrates without the significant drawbacks involved in conventional methods of the art. Such knowledge could eventually prove useful for favorably promoting or inhibiting the growth of select microbes in a microbial population.

SUMMARY OF THE INVENTION

In one aspect, the invention is directed to a patterned polymer composition useful in cell capture. In the composition, the patterned polymer is affixed to a solid substrate, and a cell-targeting agent is attached to the patterned polymer. In order to permit effective cell capture, the cell-targeting agent is exposed (i.e., accessible) to the microbe-containing environment. In particular embodiments, the cell-targeting agent is a lectin. A particular advantage of lectins is that they are capable of specifically recognizing (and hence, selectively targeting) extracellular oligosaccharide moieties, thereby offering a nondestructive method for compositional and/or functional characterization of microbial exopolysaccharides. In some embodiments, the lectins are attached to the solid substrate by a block-copolymer. The block-copolymer may be, for example, poly(glycidyl methacrylate)-block-4,4-dimethyl-2-vinylazlactone ("PGMA-b-PVDMA"), which can be employed as a surface scaffold for lectin-specific microbial capture. In some embodiments, the patterned polymer has a three-dimensional topography, which can improve cell capture by providing a higher contact area. In some embodiments, the three-dimensional topography suitably modifies the confinement of the cells and/or promotes microbe-microbe interactions.

In another aspect, the invention is directed to a liquid or gas testing device in which the above-described cell-targeting composition is incorporated. The device can be, for example, any of the flow through devices known in the art useful in conducting assays on a liquid or gas sample.

In another aspect, the invention is directed to a method of capturing cells by contacting the cell-capturing composition or device described above with cells that may be in a liquid or gaseous medium. In particular embodiments, the cell-containing (or more particularly, microbial-containing) medium is passed through a flow-through device containing the above-described capturing composition.

In yet other aspects, the invention is directed to methods for preparing the capturing composition and/or device into which the composition is incorporated. The method typically includes lithographic patterning of a polymer having a cell-capturing agent attached thereto. In particular embodiments, the method includes lithographic patterning of a polymer on a substrate, wherein the polymer is covalently bound to the substrate and contains functional groups for binding to a cell-capturing agent, followed by covalently binding the cell-capturing agent to the polymer.

DETAILED DESCRIPTION OF THE INVENTION

Figure 1:
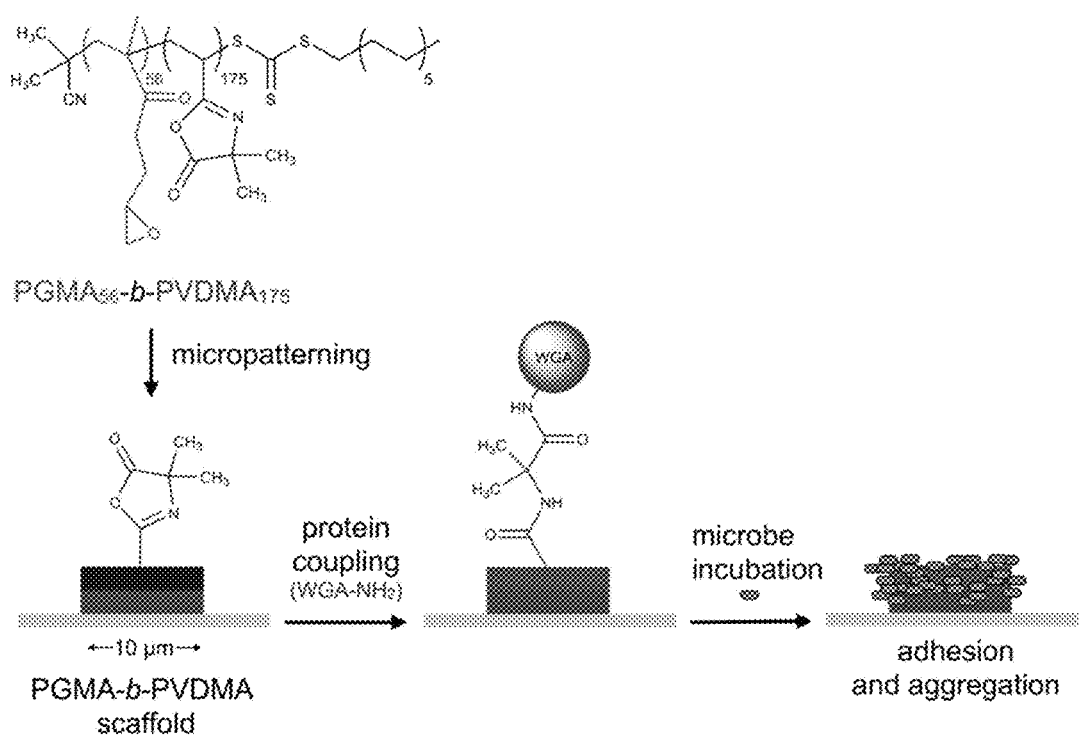
FIG. 1. Schematic showing a general approach for micropatterning a layer of PGMA-b-PVDMA polymer, coupling a lectin thereto, and use of the patterned lectin-functionalized scaffold for microbial capture.

In the cell-capturing composition, a patterned polymer is affixed (i.e., attached, generally by covalent means) to a solid substrate. The term "patterned", as used herein, generally refers to the presence of topographical features having a height or depth of at least 1, 2, 3, 4, 5, 10, 20, 50, 100, 200, or 500 nm, or within a range therein, as could be provided by a lithographic method. The topographical features can be of any shape, and may be outward-facing (i.e., above the base polymer surface) or inward-facing (i.e., below the base polymer surface, as an indent or trench). The outward- or inward-facing features may be, for example, linear segments, pillars, cones, posts, or a circular or polygonal shape (e.g., triangle, square, pentagon, hexagon, or octagon) having a height or depth in the nanometer range, as well as regular or random arrays of such shapes. Some exemplary shapes include lines and square grids. In some embodiments, the patterned polymer can have a three-dimensional structure. The term "three dimensional structure," as used herein, generally refers to a polymeric material having a structure beyond that of a monolayer of a polymer brush (i.e., a multilayer structure), generally with protruding features having heights (i.e., from the polymer base) beyond that of a monolayer of a polymer brush, i.e., generally at least or greater than 500 nm, 600 nm, 700 nm, 800 nm, 900 nm, 1 μm, 1.5 μm, 2 μm, 2.5 μm, 3 μm, 3.5 μm, 4 μm, 4.5 μm, or 5 μm, or a value within a range bounded by any two of these values. The length and/or diameter of the features (i.e., along the plane of the substrate surface) may be any of the values provided above for the height or depth, and may or may not also extend into higher values of the micron scale, e.g., at least, greater than, up to, or less than 10, 20, 30, 40, 50, 100, 200, or 500 μm. In some embodiments, the polymer possesses a three-dimensional structure on a relatively flat substrate surface. In other embodiments, the polymer possesses a three-dimensional structure by being affixed to a substrate with a defined three-dimensional structure. In yet other embodiments, the polymer possesses a three-dimensional structure distinct from a separate three-dimensional structure possessed by the substrate.

The patterned polymer may be varied in terms of its pitch. The term "pitch", as used herein, is an indication of the frequency of features (e.g., protrusions or indentations) per unit length or area. The frequency of features can be expressed as a distance between features (e.g., line center to line center distance), or may be expressed as a frequency of features per unit length or area. The term "pitch" may herein be understood to be equivalent to the term "pattern density", which may more generally refer to the number of features per area. In some embodiments, the term "pitch" refers to the line spacing between features, whereas the term "pattern density" refers to the number of features per unit length or area, in which case a decrease in pitch corresponds to an increase in pattern density, and vice-versa. Generally, when the term "pitch" or "pattern density" is applied, the features are regularly spaced. The variation of pitch may be applied to any shape of the patterned polymer, including line and square shapes. In some embodiments, the patterned polymer possesses a pitch of about, at least, above, up to, or less than, for example, 0, 1, 2, 5, 7, 10, 15, 20, 25, 30, 35, 40, 45, 50, 60, 70, 80, 85, 90, or 100 μm, or a value within a range bounded by any two of the foregoing values. Any of foregoing pitch values may be taken as or correspond to (i.e., by appropriate calculation) a pattern density. One advantage of tuning the pitch of the patterned polymer is that it results in a change in the aggregation of the microbes that interact with the cell-targeting agent. FIGS. 8-10 provide an illustration of tuning the pitch of the patterned polymer that can result in a dramatic effect on the aggregation of microbes.

The patterned polymer can have any composition and structure, provided that it is stable under the conditions used, e.g., insoluble and non-degradable in an aqueous medium if used in such a medium. A variety of commercial substrates are available that contain surface polymers that can be modified with secondary molecules in an aqueous medium. For example, NETERION® Slide H covalently immobilizes peptides and proteins, such as antibodies, antibody fragments, enzymes or receptors, on a dedicated slide surface. The polymer can be a homopolymer or copolymer (which may be a bipolymer, terpolymer, tetrapolymer, or higher functional polymer), either of which may be linear or branched, wherein the branched polymer may also be a star, brush, or comb type of branched polymer. In the case of a copolymer, the copolymer can be, for example, a block, alternating, periodic, random, or graft copolymer. The polymer can have any suitable number of units, such as at least, above, up to, or less than, for example, 10, 25, 50, 100, 200, 300, 400, 500, 1000, 5000, 10,000, or more units.

The polymer is typically one that can either be grown on or facilely coated onto the surface of a solid substrate. The polymer can be, for example, a vinyl addition polymer (e.g., a polyacrylate, polymethacrylate, poly(methyl acrylate), poly(methyl methacrylate), polystyrene, polyvinylchloride, and the like), polyester, polyurethane, polyamide, epoxide (as derived from an epoxy resin), or polyimide. Before attachment to the solid substrate, the polymer preferably contains functional groups that can react with and form permanent bonds (e.g., covalent bonds) with groups found on the substrate surface. For example, in the case where the substrate surface contains hydroxy groups, the polymer may contain suitable hydroxy-reactive groups, such as epoxy or isocyanate groups, or the substrate surface may be functionalized with epoxy, carboxy, or isocyanate groups in the event the polymer contains hydroxy or amino groups. Moreover, the polymer may be a single polymer or a combination of polymers, wherein a combination of polymers may be within a single layer as a mixture, or may be constructed of two or more layers of different types of polymers. In the case of multiple layers, the polymer layers should be attached to each other without release during cell capture.

The patterned polymer may have any suitable thickness, which is herein defined as the distance from the substrate surface (in contact with the polymer) to polymeric features of maximum height. In different embodiments, the patterned polymer possesses a thickness of about, at least, above, up to, or less than, for example, 1, 2, 5, 10, 20, 30, 40, 50, 100, 200, 300, 400, 500, 600, 700, 800, 900, 1000, 2000, 3000, 4000, 5000, or 10,000 nm, or a value within a range bounded by any two of the foregoing values. In one embodiment, the thickness of the patterned polymer is from 75 nm to 10 µm. In another embodiment, the thickness of the patterned polymer is from 115 nm to 2 µm. In another embodiment, the thickness of the patterned polymer is from 250 nm to 10 µm. In yet another embodiment, the thickness of the patterned polymer is from 500 nm to 2 µm.

A particular advantage of the patterned polymer described herein is its high level of polyvalency, i.e., large number of reactive groups per unit area, which results in an enhanced performance of the cell-targeting agent. Further improvements are herein made possible by use of the specially crafted surface topography described above, along with the patterned polymer thickness, the choice of patterning, and the pitch of the patterned polymer.

The cell-targeting agent is attached to the patterned polymer. The cell-targeting agent can be attached by any bonding mode that retains the cell-targeting agent on the patterned polymer at least up to cell capture. The cell-targeting agent may be bound to the patterned polymer by, for example, covalent bonding, ionic bonding, hydrogen bonding, or affinity bonding. The cell-targeting agent is any substance capable of binding to a cell. Since exopolysaccharides (i.e., "EPS") are found on the surfaces of most cells, the instant disclosure particularly considers cell-targeting agents that target EPS, such as carbohydrate-binding proteins. Some particular carbohydrate-binding proteins considered herein are the lectins. The lectin can be any of the lectins known in the art, including lectins that have been modified to selectively bind to specific types of EPS or cells, or a lectin fragment. The lectin or lectin fragment can be, for example, a mannose-binding, galactose-binding, N-acetylgalactosamine-binding, N-acetylglucosamine-binding, N-acetylneuraminic acid-binding, or fucose-binding type of lectin. The lectin may also be derived from a specific source, such as wheat germ agglutinin (WGA), concanavalin A, lentil lectin, peanut agglutinin, or elderberry lectin. Other cell-targeting agents may or may not include antibodies or antibody fragments. Yet other cell-targeting agents may or may not include RNA and DNA aptamers, as described in *J. Sep. Sci.*, 32(10):1523-30, 2009, the contents of which are herein incorporated by reference. Further examples of cell-targeting agents may or may not include extracellular matrix proteins, such as collagen, laminin and fibronection, as well as carbohydrates, oligosaccharides, and polysaccharides, as described in *J Am. Chem. Soc.*, 133:13957-13966, 2011, the contents of which are herein incorporated by reference. In the case where the cell is a microbe, or more particularly, a bacteria, the cell-targeting agent can be considered to be a microbe-targeting or bacteria-targeting agent.

The cell-targeting agent needs to be exposed so that it is accessible to the cell. The term "exposed", as used herein, generally means that the cell-targeting agent resides on the surface of the patterned polymer and is not covered by or embedded within the polymer or other solid substance.

The solid substrate on which the patterned polymer is coated can be made of any material on which a polymer can be attached and patterned, and which is amenable and non-reactive with substances in which it comes into contact during the cell capture process. The substrate can be, for example, metallic (e.g., metal or metal alloy, generally corrosion resistant and non-reactive), semiconductor, metal oxide, or plastic. The term "metallic", as used herein, is also meant to encompass those compositions that may include one or more non-metal elements (e.g., carbon, silicon, nitrogen, or boron), but which maintain substantial metallic character, e.g., metal carbides, silicides, nitrides, and borides. The term "semiconductor" is meant to encompass all of those materials known in the art to have semiconducting properties, including, for example, silicon and germanium, and their nitride, phosphide, sulfide, selenide, and telluride compositions, as well as related compositions based on boron, aluminum, gallium, indium, arsenic, and antimony (e.g., aluminum, gallium, and indium nitrides, phosphides, arsenides, sulfides, selenides, and tellurides). The term "metal oxide", as used herein, is also meant to encompass ceramic and hybrid organic-inorganic materials. In particular embodiments, the metal oxide is or includes silicon oxide (silica), cerium oxide (ceria), yttrium oxide (yttria), titanium oxide (titania), zirconium oxide (zirconia), indium oxide, tin oxide, indium tin oxide, hafnium oxide, spinel oxide, or a perovskite oxide, or a combination thereof.

In another aspect, the invention is directed to methods for producing the cell-capture composition described above. In the method, a polymer is first coated onto a solid substrate by any of the means known in the art. For example, the substrate surface can be spin coated, spray coated, or dip coated by means well known in the art. The method for coating the polymer should include means for the polymer to become permanently bound to the solid substrate, typically by covalent bonding. Other bonding modes, such as ionic, hydrogen bonding, or affinity bonding (e.g., by biotin-avidin coupling) may also be possible, provided the polymer does not detach from the solid substrate during use. In particular embodiments, the surface of the solid substrate possesses, or is made to possess, functional groups that can be reacted with and form covalent bonds with the polymer. For example, the solid substrate may be made to possess oxygen-containing functional groups (e.g., hydroxy and/or carboxylic acid) by treatment in an oxygen plasma. Such surface functional groups can be reacted with suitably reactive groups (e.g., epoxy, activated ester, anhydride, isocyanate, or amino groups) on the polymer.

Various methodologies can be used to introduce nanoscale, microscale, or three-dimensional features into the polymer to result in a patterned polymer. The patterning method is typically based on photolithography, but may be another method known in the art capable of producing such features, such as self-assembly or scribing methods. In a first embodiment, the substrate surface is patterned with reactive functional groups, such as by pattern masking followed by oxygen plasma, and the patterned surface reacted with the polymer to provide a patterned polymer. In a second embodiment, the polymer is coated onto an unpatterned substrate, and the polymer, as coated, is patterned by means known in the art, e.g., the polymer may include positive or negative resist groups that can be activated during a photolithographic, ultraviolet, or electron beam exposure process, and then developed. In a third embodiment, a mask, which is a removable material that selectively protects the underlying substrate, is coated and patterned onto a substrate. The polymer is then coated onto the patterned mask and substrate. Upon removal of the mask, the polymer is selectively left behind on the substrate in the regions unprotected by the mask. The foregoing process can be referred to as a "lift-off process".

The cell-targeting agent can be attached to the patterned polymer by means well known in the art. In one embodiment, functional groups reactive with the cell-targeting agent are in the polymer when the polymer is coated onto the substrate; after coating the polymer, the cell-targeting agent is reacted with the patterned polymer to form covalent or other permanent bonds therewith. For example, in the case of a lectin or antibody cell-targeting agent, the polymer may contain protein-binding groups therein, such as lactone groups (or more specifically, azlactone groups), activated ester groups, maleimide, or phenyl azide groups for covalent binding to the lectin or antibody. In another embodiment, the polymer is coated onto the substrate and then functionalized with functional groups reactive with the cell-targeting agent, before or after patterning, and the cell-targeting agent reacted with the patterned polymer to form covalent or other permanent bonds therewith. The functionalization of such polymers is well known in the art.

The patterned polymer can be modified to maximize the concentration of cell-targeting agent that is attached to the patterned polymer. This can be realized by, for example, optimizing block length, composition, and/or film thickness of the patterned polymer.

In another aspect, the invention is directed to a cell capture device into which the above-described cell capture composition is incorporated. The cell capture composition is incorporated in the device in such a manner that a liquid or gas being tested makes contact with the cell capture composition. The cell capture device can have, for example, any of the flow through designs and components known in the art for testing of fluid or gaseous samples. In some embodiments, the capture device operates by any of the gravity-assisted vertical flow or lateral flow designs known in the art, such as those used in Coulter counters. Reference is made to, for example, U.S. Pat. Nos. 3,922,203 and 5,139,031, the contents of which are herein incorporated by reference in their entirety. In some embodiments, the capture device is a microfluidic device, as well known in the art, e.g., K. Leung, et al., *PNAS*, vol. 109, no. 20, pp. 7665-7670 (2012) and S. A. Hashsham, et al., *Microbe*, vol. 2, no. 11, pp. 531-536 (2007), the contents of which are herein incorporated by reference in their entirety. The capture device may also be a multi-platform flow device, as described in, for example, M. C. Hesselman, et al., *PLOS ONE*, vol. 7, no. 5, pp. 1-8, May 2012, the contents of which are herein incorporated by reference in their entirety.

In another aspect, the invention is directed to a method of cell capture by use of the cell-capturing composition or device described above. In the method, the cell capture composition is contacted with a liquid or gaseous medium to be analyzed. If the cell capture composition is incorporated into a device, the device includes the necessary and/or optional components, as well known in the art (e.g., filters, channels, wells, micropumps, valves, and the like) for directing or channeling the fluid or gas to the cell capture composition. In some embodiments, the liquid or gaseous medium to be analyzed is known to contain cellular material, whereas, in other embodiments, the liquid or gaseous medium may not be known to contain cellular material or a particular cellular material being sought, but is being tested to determine if such cellular material is present. In the case of a liquid sample, the liquid may be from any source in which cellular material may reside. The liquid may be, for example, a biological fluid (e.g., saliva, blood, urine, mucus, or ocular fluid) from an organism, such as a mammal, and more particularly, a human. The liquid may alternatively be from a non-living source, such as an industrial or sewage waste stream, or a natural source, such as a water spring, aquifer, lake, pond, or the deep sea. A gaseous sample may also be from any of the sources mentioned above, or may be air sampled from within a manmade structure (e.g., a home or industry) or from the outdoors.

The term "cell", as used herein, refers to the basic structural building block of living organisms having at least a cell membrane (which may be a cell wall, in the case of a plant) that encloses a protoplasm and organelles. For purposes of the instant invention, the cell particularly considered herein is one that contains exopolysaccharides on its surface. The cell may have a cell nucleus (i.e., a eukaryotic cell) or lack a cell nucleus (i.e., a prokaryotic cell). Moreover, the term "cell", as used herein, may refer to a single cell (i.e., monocellular) or a multiplicity of cells that may be agglomerated or that may form a microscale multicellular organism, wherein the unicellular or multicellular organism under consideration is typically no more than about 100 microns in size. In one embodiment, the cell is a mammalian cell, which may be from any bodily tissue or fluid, including cancerous or pre-cancerous tissue. In another embodiment, the cell is a living organism, i.e., a microbe, which may be, for example, a bacterium, fungus (e.g., mold spore), protist, or plant cell. In some embodiments, the cell being captured may not be living, such as in a dormant or dead state. In particular embodiments, the cells being targeted are pathogenic and possibly infectious microbes, such as those belonging to *Streptococcus, Staphylococcus, E. Coli, mycobacteria, Helicobacter pylori, Pseudomonas aeruginosa, Salmonella,* and *Chlamydia*.

The term "cell capture", as used herein, refers to a binding interaction between the immobilized cell-capturing agent and the cell. The binding interaction may occur by any of the known binding modes, e.g., covalent, ionic, hydrogen bonding, or affinity bonds. In some embodiments, the binding interaction is temporary (i.e., is followed by release), while in other embodiments, the binding interaction is permanent. In the case of a temporary interaction, in a first embodiment, the temporary interaction is of sufficient time to permit study of the captured cells in the captured state (followed by subsequent release), while in a second embodiment, the temporary interaction is of sufficient time only for the cell to deposit a substance or react with the capture agent or other aspect of the polymer, with subsequent study of the deposited or reacted cellular substance and not the captured cell itself. In some embodiments, the interaction may function to modify aspects of the cell, e.g., to activate or deactivate cell growth, promote or reduce cell adhesion, modify mammalian cell chemotaxis, alter cell population distributions, or promote cell death, any of which may or may not be selective to particular cell types within a distribution of cell types.

In some embodiments, the polymer is functionalized with additional functional groups, in addition to the cell capture agent, that augment or suitably modify the efficacy, selectivity, or function of the cell capture agent. The additional functional groups may be, for example, another (different) cell capture agent (e.g., a combination of specific and non-specific cell capture agents, or two different specific capture agents), or a group that does not function as a cell capture agent but has a desired effect on the cell capture agent. For example, the polymer may include protein-coupling groups that are made to couple to more than one cell-targeting protein, or couple to a combination of a specific cell-targeting protein and a non-specific protein, such as bovine serum albumin (BSA). These embodiments may be particularly advantageous in that the additional functional groups can be included in amounts that manipulate the lectin surface concentration to result in tunable or selective cell capture. In some embodiments, the additional functional groups can be anti-microbial (e.g., anti-bacterial) agents, such as any of the small peptides and other molecules (e.g., quaternary ammonium salts) known for this purpose, e.g., Yu et al., "Nanopatterned smart polymer surfaces for controlled attachment, killing, and release of bacteria", *ACS Appl. Mater. Interfaces,* 5(19):9295-304 (2013), the contents of which are herein incorporated by reference in their entirety. By including anti-microbial agents, the resulting cell-capture composition can function as a biocidal surface (and in particular embodiments, a selective biocidal surface) that can kill microbes captured from a community of microbes. In other embodiments, the additional functional groups may be fluorophores or chromogenic in nature, in which case the presence of a particular type or species of cell or microbe may be detected by a change in the fluorophore or color intensity or wavelength upon capture of the cell or microbe. In yet other embodiments, the additional functional groups may be enzymatic groups that elicit an observable change in color or other spectroscopic signature upon cell capture, or that desirably alter cell growth.

In one embodiment, the cell-targeting agent can be selected to target a broad range of cells. In another embodiment, the cell-targeting agent can be selected to target specific types of cells, or a particular genus or species of bacteria or other microbe.

The patterned or three-dimensional structure of the polymer endows the polymer with a significantly greater ability to capture and retain cells as compared to an unpatterned version of the polymer. Without being bound by any theory, it is believed that cells are significantly more inclined to bind to sharp vertices or edges of the patterned features as compared to smooth parts of the polymer. Thus, by inclusion of such features, a significantly greater cell capture density has been realized.

FIG. 1 is a schematic showing a particular embodiment in which a layer (which may be a monolayer, bilayer, trilayer, or higher multilayer) of a PGMA-b-PVDMA polymer is micropatterned, followed by coupling to a lectin, and use of the patterned lectin-functionalized scaffold for microbial capture. In the scheme shown in FIG. 1, the azlactone protein-coupling group may be replaced with any other suitable protein-coupling group, and the epoxy group may be replaced with any other suitable reactive group capable of bonding with the solid substrate. The polymer may also possess a different polymeric backbone than shown, i.e., may or may not have a vinyl addition backbone, and may or may not be produced by RAFT polymerization. Moreover, the cell-capture agent may be other than a lectin, and the microbe being captured may be a non-microbial cell.

Examples have been set forth below for the purpose of illustration and to describe certain specific embodiments of the invention. However, the scope of this invention is not to be in any way limited by the examples set forth herein.

EXAMPLE 1

Materials

Wheat germ agglutinin conjugated with Alexa Fluor® 488 (WGA-A488; Invitrogen) and *Lens culinaris* lectins conjugated with Texas Red isothiocyanate (WGA-A488-TRITC; EY laboratories) were diluted to 1 mg/mL concentrations in 1× PBS and stored at −20° C. Four-inch silicon (Si) wafers were used. Poly(glycidyl methacrylate)-block-poly(vinyldimethyl azlactone) (PGMA-b-PVDMA) of block lengths of 56 and 175, respectively, were synthesized as previously described (Lokitz, B. S., et al., *Macromolecules,* 2012, 45, pp. 6438-6449). *Pseudomonas fluorescens* GM30, a gram negative PGPR that plays a role in plant pathogen protection, was isolated from the *Populus deltoides* rhizosphere and used in this study as a model microbe (Weston, D. J., et al., *Molecular Plant-Microbe Interactions,* 2012, 25, pp. 765-778; and Brown, S. D., et al., *Journal of Bacteriology,* 2012, 194, 5991-5993). This microbe was stored in glycerol stocks at −80° C. until use.

Lithographic Patterning of PGMA-b-PVDMA and Si Control Scaffolds

Silicon wafers were spin coated with Shin-Etsu MicroSi MicroPrime™ P20 at 3000 rpm for 45 s, followed by S1818 (Microchem Corp.) positive resist at 3000 rpm for 45 s and baked on a hot plate at 115° C. for 60 s. Wafers were then exposed for 6 s with a contact mask aligner and developed in CD-26 for 2 min., rinsed with DI H$_2$O, and dried with nitrogen. Wafers were then treated with oxygen (O$_2$) plasma using a Tepla Ion Wave 10 plasma processing system to remove residual resist and diced into 10×10 mm substrates. Wafers contained arrays of spots 10 or 50 μm in diameter with a pitch of 20 or 100 μm, respectively. Prior to spin coating, substrates were again treated with 3 min. of oxygen plasma to provide surface hydroxyl groups for reaction with epoxy groups present on the PGMA block. 100 μL of a 1 wt % solution of PGMA56-b-PVDMA175 in anhydrous CHCl$_3$ was then spin-coated over the substrate (Laurell WS-400B-6NPP/LITE) at 1500 rpm for 15 s and baked at 110° C. under vacuum for 18 hrs to allow for microphase segregation and surface attachment. Substrates were sonicated in acetone for 5 min, rinsed in isopropanol, and dried with nitrogen to remove photoresist. Patterned substrates were stored under vacuum in a desiccator until use.

For the fabrication of Si posts, identical patterns were used. Silicon wafers were spin coated with Shin-Etsu MicroSi MicroPrime™ P20 at 3000 rpm for 45 s followed by JSR NFR-016D2 55 cp negative resist at 3000 rpm for 45 s, baked on a hot plate at 90° C. for 90 s. Wafers were then exposed for 3 s using a contact mask aligner, baked on a hot plate at 115° C. for 90 s and developed in CD-26 developer for 1 min. Wafers were etched as previously described (Walker, B. N., et al., *J. Phys. Chem. C*, 2010, 114, pp. 4835-4840) using an Oxford Plasmalab 100 reactive ion etching system to provide posts of heights of 1-2 μm. After etching, substrates were diced into 10×10 mm substrates and cleaned with Piranha solution to remove residual resist material.

Lectin Functionalization of Patterned Substrates

Substrates containing PGMA-b-PVDMA scaffolds or Si control scaffolds were contacted with 100 μL of 1 mg/mL solutions of WGA-A488 lectin, LcH-TRITC lectin, or BSA in 1× PBS for varied incubation times in a humidified environment. After protein functionalization, substrates were washed for 5 min with a 0.05% solution of Tween 20 in 1× PBS and then stored in 1× PBS until further use. In control experiments where it was desired to block protein coupling to the PGMA-b-PVDMA scaffolds, substrates were submerged in a solution of 50 mM ethanolamine in 50 mM borate buffer, pH 8.5, for 18 hours prior to protein incubation.

Bacterial Culture and Adhesion Conditions

*Pseudomonas fluorescens* GM30 was used in this study. Microbes were cultured on tryptone yeast (TY) agar plates (10 g tryptone, 5 g yeast extract, 15 g agar per liter) for 24-48 hours at 28° C. and then maintained at ambient conditions for up to one week. For growth in liquid, a single colony was used to inoculate liquid TY media in sterile 20 mL glass tubes. The microbes were grown to logarithmic phase in a shaking incubator set at 28° C. and 200 rpm, harvested by centrifugation, and resuspended in 1× PBS at an OD$_{600}$ of 0.1. A 100 μL aliquot of the microbe solution was incubated onto protein functionalized substrates in a humidified environment for 1 hour under gentle rocking. To remove unattached microbes, substrates were washed for 5 min with a 0.05% solution of Tween 20 in 1× PBS. The remaining adherent microbes were then chemically fixed to the surface by incubating the substrate in a 2.5% solution of glutaraldehyde in H$_2$O. Finally, the substrates were dried by gently aspirating the water off the surface.

Analysis

Brightfield and Fluorescence Microscopy. All images of silicon substrates containing arrays of PGMA-b-PVDMA or Si supports were taken in brightfield or fluorescence (20×, NA 0.40/50×, NA 0.85/100×, NA 0.95) with an upright microscope (BX51, Olympus). For characterizations of microbial adhesion levels on the substrates, 20 to 30 representative images of each substrate were taken near the center of the 10×10 mm arrays.

Atomic Force Microscopy. An atomic force microscope (Park Systems) was used to image the PGMA-b-PVDMA patterns. NanoWorld® PNP-TR B cantilevers with a resonance frequency of 17 kHz and a force constant of 0.08 N m$^{-1}$ were used in contact mode. Scan areas were varied between 4 and 1600 μm$^2$. Images were captured at a scan rate of 0.2-0.6 Hz. Support heights and surface roughness were analyzed using Park software.

Fourier Transform Infrared Spectroscopy. Polymer films were characterized using a Harrick Scientific VariGATR instrument with a germanium crystal and a MCT detector. Spectra were analyzed using OPUS software. The crystal was cleaned with methanol prior to each sample. A background spectrum was collected using 128 scans, and samples were collected as the average of 512 scans. All spectra were baseline corrected.

Image Analysis

All images were analyzed using ImageJ software. Fluorescent signal intensities for WGA-A488 lectin functionalized PGMA-b-PVDMA supports were averaged across 100 replicate spots. Microbial adhesion levels on PGMA-b-PVDMA or Si supports were analyzed using image thresholding by the triangle method. To quantify the microbial growth from the support exterior, the increase in support area with microbial deposition was measured. 200 representative surface supports were measured under each condition investigated.

Statistical Analysis of Data

All data is reported as the mean±standard deviation from replicate measurements. The Statistical Analysis Toolbox in MATLAB was used for all statistical tests. Differences between microbial surface coverage on different substrates was identified using the student t-test ($p<0.01$).

Results and Discussion

Figures 2A, 2B, 2C:
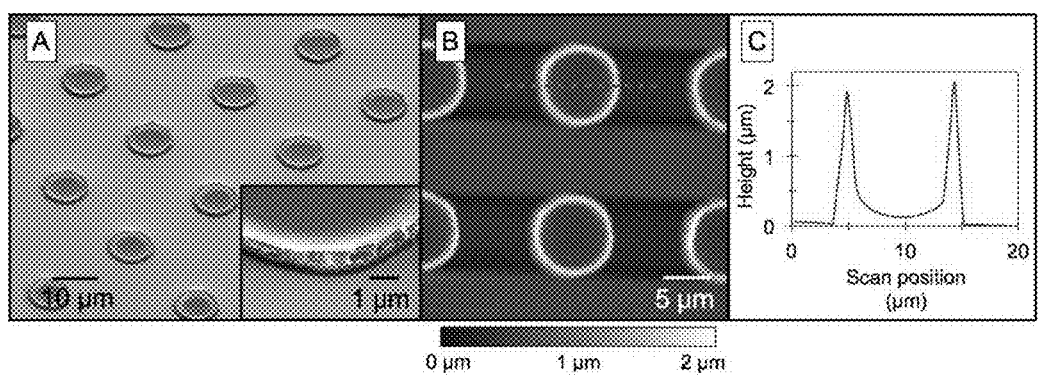
FIGS. 2A-2C. Microscopic images of 10 μm diameter PGMA-b-PVDMA patterned polymers. (A) 50× scanning electron microscope (SEM) image (B) AFM contact mode image and (C) cross-sectional height profile across the center of a scaffold corresponding to the dashed line in (B).

The lithographic patterning of PGMA-b-PVDMA onto oxidized silicon surfaces resulted in well defined, three dimensional co-polymer surface structures of 10 μm diameter, as shown in the 50× SEM images in FIG. 2A. A smooth PGMA-b-PVDMA exists in the interior of the scaffold, while the outer edge regions exhibit higher surface roughness, as apparent in the insert in FIG. 2A. The microphase segregation of the PGMA and PVDMA blocks during the annealing step advantageously resulted in a PGMA-rich interior at the substrate interface for covalent surface attachment and a PVDMA-rich exterior region for secondary functionalization. After fabrication, all PGMA-b-PVDMA supports remained on the silicon substrate through washing steps in organic or aqueous solvents. The AFM image in FIG. 2B and the cross-sectional height profile in FIG. 2C (across the center of a scaffold corresponding to the dashed line in FIG. 2B) show varied internal film thickness with respect to radial direction resulting from patterning using the liftoff process. At the support center, film thickness is minimal, with an average thickness of 115±32 nm. This value approaches the expected thickness for a single layer of PGMA-b-PVDMA films (Lokitz et al., 2012, Ibid.). Moving from the center towards the exterior of the support, the film thickness increases non-linearly and is maximum at the edges where the polymer thickness ranges between 500 nm to 2 µm. The formation of stable polymer structures at higher film thicknesses (greater than 90 nm) is influenced by the height of the templating photoresist, and is likely due to the crosslinking of GMA blocks away from the substrate interface, which is favored using an annealing temperature of 110° C. Annealing at temperatures <80° C. has been shown to eliminate GMA crosslinking while still promoting surface attachment (Lokitz et al., 2012, Ibid.). Thus, it is likely that lower annealing temperature combined with higher diameter posts would favor a single PGMA-b-PVDMA layer of minimal surface height variation.

Lectin Coupling to PGMA-b-PVDMA Surface Supports

Figures 3A, 3B:
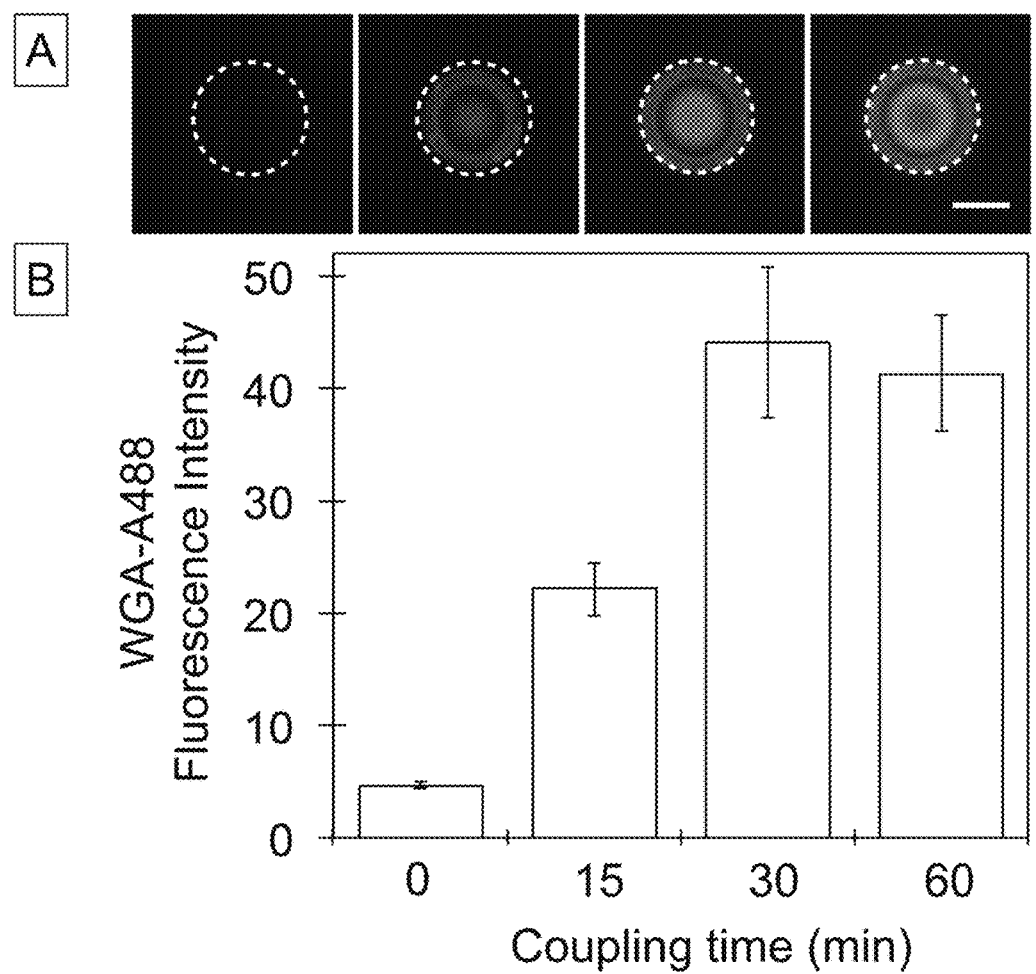
FIGS. 3A, 3B. Lectin capture onto PGMA-b-PVDMA patterned polymers. (A) Representative 100× fluorescence images of PGMA-b-PVDMA patterned polymers after modification with WGA-A488 lectin at incubation times of 0, 15, 30, and 60 minutes (left to right). In each image from left to right, the white outer circle indicates the location of the PGMA-b-PVDMA patterned polymers (scale bar=5 μm). B) Fluorescence intensity values of PGMA-b-PVDMA patterned polymers after treatment with WGA-A488 lectin for the different incubation times.

To investigate the covalent coupling of lectin proteins, WGA-A488 lectin was incubated onto patterned surfaces containing 10 µm diameter PGMA-b-PVDMA surface supports and then imaged using fluorescence microscopy. FIG. 3A displays the fluorescence intensities achieved from WGA-A488 lectin coupling to the PGMA-b-PVDMA surface supports under different incubation times. FIG. 3B shows the corresponding fluorescence intensity values for the different incubation times. As shown by FIGS. 3A and 3B, after 30 min of coupling, the supports appear brightly fluorescent, with a 10-fold increase in fluorescence signal intensity relative to unmodified PGMA-b-PVDMA supports. Further incubation times did not increase the fluorescent signal, suggesting that the supports are saturated with protein between 15 and 30 min. The high fluorescence signal of the PGMA-b-PVDMA supports relative to the silicon background apparent in the fluorescence images in FIG. 3A is likely due to the high concentration of pendant VDMA groups in the support, which results in higher levels of WGA-A488 lectin immobilized over the supports.

Figures 4A, 4B:
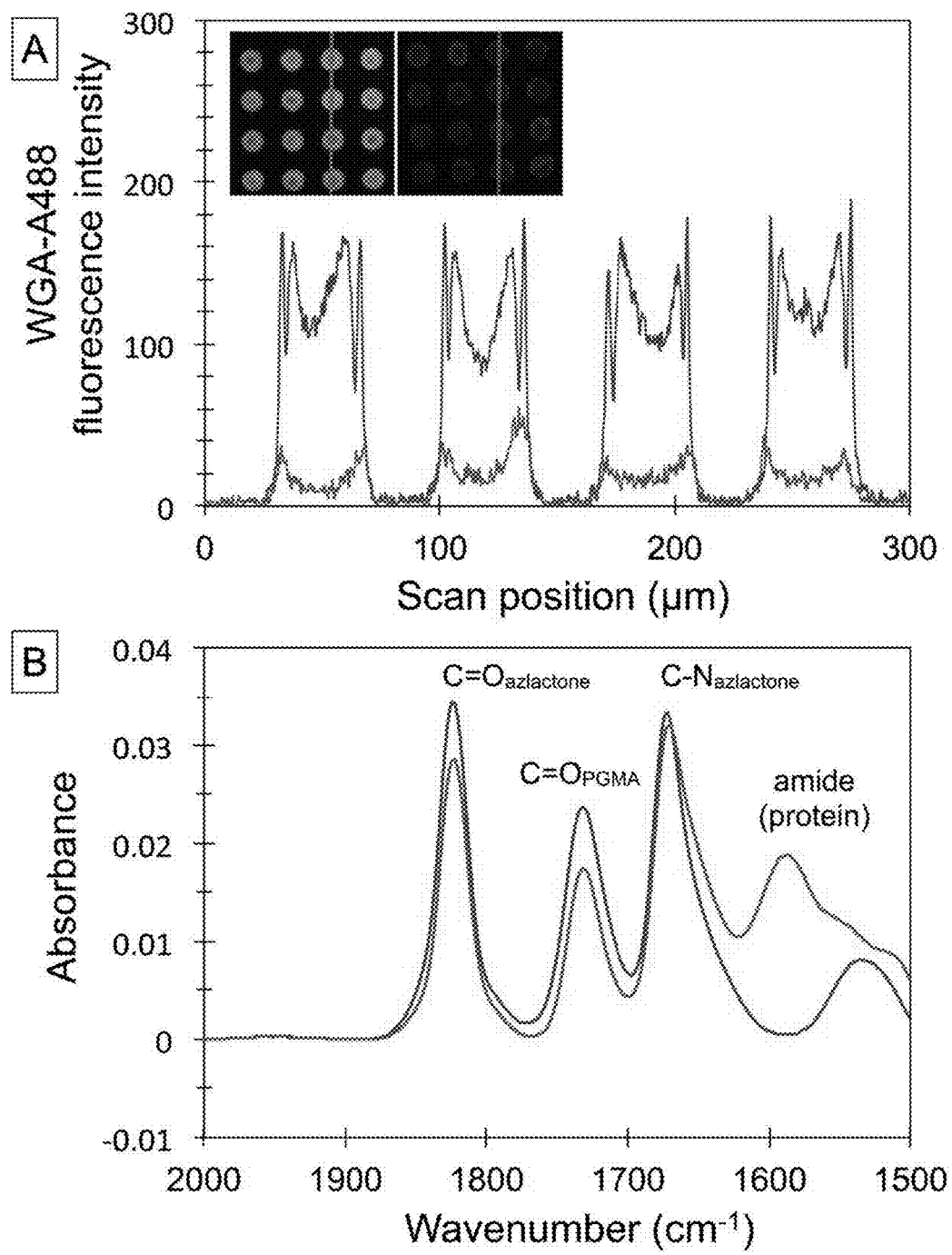
FIGS. 4A, 4B. Characterization of lectin coupling into PGMA-b-PVDMA patterned polymers. (A) Fluorescence intensity profiles of WGA-A488 lectin coupled onto PGMA-b-PVDMA patterned polymers containing functional VDMA groups or aminolysed VDMA groups. (Inset: corresponding fluorescence images) (B) Partial GATR-FTIR spectra of PGMA-b-PVDMA patterned polymers with and without WGA-A488 lectin functionalization.

The covalent immobilization of WGA-A488 lectin onto the VDMA groups was also verified. Prior to WGA-A488 lectin functionalization, a PGMA-b-PVDMA array was submerged into an aqueous solution of 50 mM ethanol amine at pH 8.5 for 18 hrs. These conditions should allow for sufficient aminolysis of accessible azlactone groups. After 30 min. of WGA-A488 lectin functionalization, an 87±1% decrease in fluorescence signal was noted when comparing supports with aminolysed VDMA groups to supports with functional VDMA groups, as shown in the fluorescent intensity profiles in FIG. 4A. This demonstrates the key role of the azlactone functionality for immobilization. GATR-FTIR was used to further characterize the functional groups present on PGMA-b-PVDMA surfaces before and after 30 min WGA-A488 functionalization. FIG. 4B shows the partial GATR-FTIR spectra of PGMA-b-PVDMA patterned polymers with and without WGA-A488 lectin functionalization. The absorbance at 1820 cm$^{-1}$, which is a measure of azlactone functionality, was specifically monitored. FIG. 4B shows a 16% decrease in 1820 cm$^{-1}$ peak height after WGA-A488 functionalization, suggesting that only a fraction of pendant azlactone groups are accessible for protein coupling. This is likely due to a collapsed structure of the VDMA blocks in aqueous buffer, limiting the diffusion of WGA-A488 proteins to internal coupling sites.

Microbial Adhesion on Lectin Functionalized PGMA-b-PVDMA Supports

The following study demonstrates that lectin-functionalized PGMA-b-PVDMA supports can be used to capture microbes based on EPS content. *P. fluorescens* GM30 was chosen as a model microbe in this study because of the high levels of visible cell clumping that were observed during later stages of liquid culture, suggesting high levels of EPS expression. WGA-A488 and LcH-TRITC were used as model capture lectins because they bound specifically to *P. fluorescens* GM30 in a solution phase lectin-binding assay, indicating the presence of extracellular GlcNAc, GalNAc, or sialic acid residues (WGA specific) as well as extracellular Mannose/GlcNAc/Fucose complex (LcH specific) in the EPS content (Hsu, K.-L., et al., *Nat. Protoc.*, 2006, 1, 543-549). BSA-functionalized PGMA-b-PVDMA supports were used as a control to measure non-specific interactions.

Figures 5A, 5B, 5C:
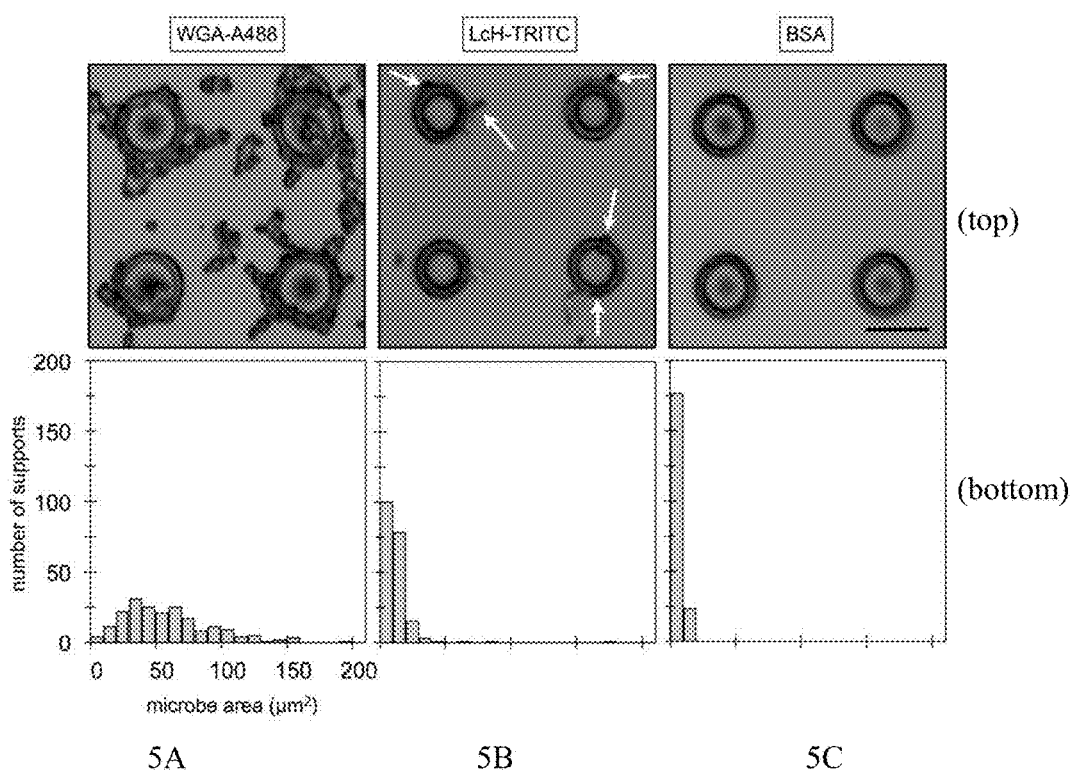
FIGS. 5A-5C. Lectin-specific microbial adhesion and flocculation around PGMA-b-PVDMA patterned polymers. 100× brightfield images of posts after incubation with microbes (top row) and corresponding histogram plots of microbial growth area from post exterior from 200 representative patterned polymers (bottom row). (A) PGMA-b-PVDMA patterned polymers with WGA-A488 lectin; (B) PGMA-b-PVDMA with LcH-TRITC lectin; and (C) PGMA-b-PVDMA patterned polymers with BSA. Arrows denote attached microbes. Scale bar=10 μm.

FIGS. 5A-5C confirm lectin-specific microbial adhesion and flocculation around PGMA-b-PVDMA patterned polymers after capture protein functionalization, microbe incubation, and washing. FIGS. 5A-5C show 100× brightfield images of posts after incubation with microbes (top row) and corresponding histogram plots of microbial growth area from post exterior from 200 representative patterned polymers (bottom row). FIG. 5A shows the results for PGMA-b-PVDMA patterned polymers with WGA-A488 lectin; FIG. 5B shows the results for PGMA-b-PVDMA with LcH-TRITC lectin; and FIG. 5C shows the results PGMA-b-PVDMA patterned polymers with BSA. The histogram plots in FIGS. 5A-5C reflect the distribution in microbe area data generated from 200 representative supports. A statistical comparison of microbe area data between WGA-A488 lectin and BSA proteins (FIGS. 5A and 5C) indicates a significant increase due to WGA-A488 lectin functionalization ($p<0.01$), which evidences WGA-specific microbial capture on the supports. The aggregation of microbes beyond the initial microbe-WGA adhesion layer in FIG. 5A is consistent with recent reports of surface-bound *Pseudomonas* species promoting the recruitment of additional microbes into microcolonies (Zhao, K., et al., *Nature*, 2014, 497, pp. 388-391). Microbes showed significantly less adhesion onto LcH-TRITC lectin functionalized PGMA-b-PVDMA supports (FIG. 5B), although an increase in adhered microbes relative to the BSA control supports was observed.

*P. fluorescens* GM30 was observed to preferentially adhere to edges of the patterned features. The preferential adhesion onto the PGMA-PVDMA support edges is likely due to the enhanced topographical surface features associated with the edge regions of the spots. In contrast, minimal adhesion is observed in the center of the supports, where the surface appears relatively smooth. A similar trend was noted on two-dimensional substrates containing micropatterned areas of covalently immobilized WGA-A488 lectin on surfaces of low roughness ($R_a=0.23±0.03$ nm), which also failed to engage *P. fluorescens* GM30 microbes under the same conditions.

Figures 6A, 6B, 6C:
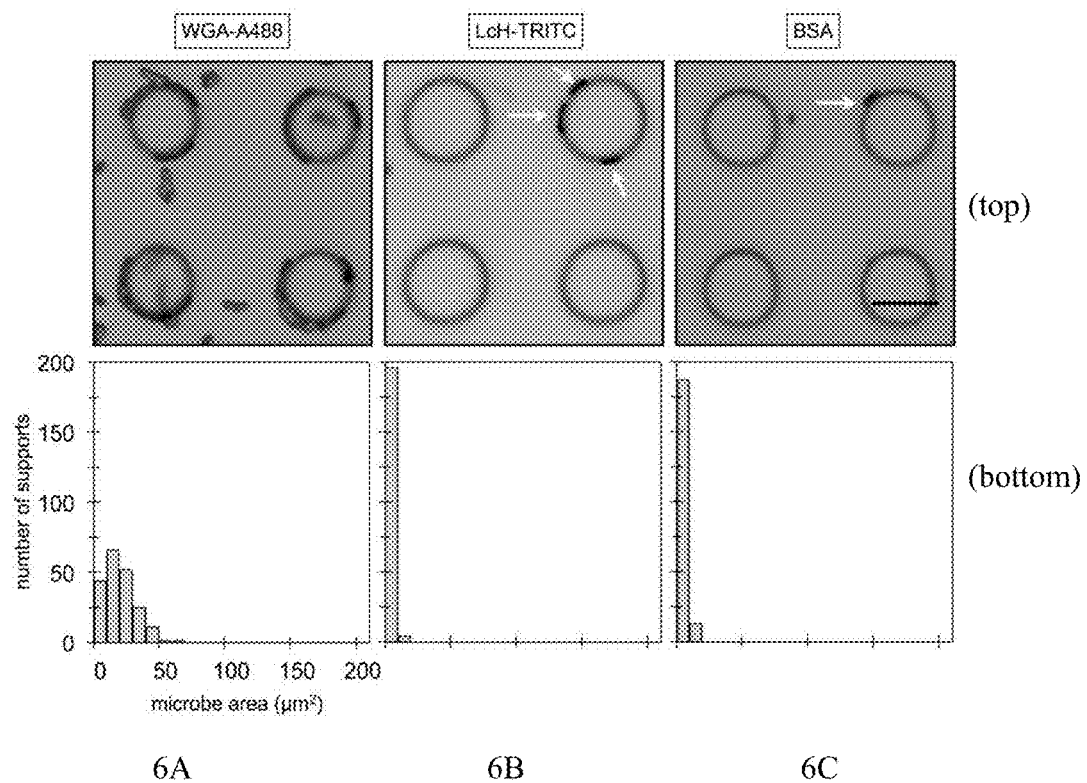
FIGS. 6A-6C. Lectin-specific microbial adhesion and flocculation around Si supports. 100× brightfield images of posts after incubation with microbes (top row) and corresponding histogram plots of microbial growth area from post exterior from 200 representative supports (bottom row). (A) Si support with WGA-A488 lectin. (B) Si support with LcH-TRITC lectin. (C) Si support with BSA. Arrows denote attached microbes. Scale bar=10 μm.

To further decipher the effect of surface topography for promoting microbial adhesion, the PGMA-b-PVDMA supports were mimicked using 10 µm diameter Si posts etched to a depth of 1.3 µm. In contrast to the PVDMA-b-PVDMA supports, although these surfaces possess comparable surface topologies, they only immobilized captured protein by passive adsorption. WGA-A488 lectin, LcH-TRITC lectin, and BSA were physisorbed onto the silicon structures, followed by microbe incubation and washing under identical conditions as with the PGMA-b-PVDMA supports. FIGS. 6A-6C show lectin-specific microbial adhesion and flocculation around Si supports. FIGS. 6A-6C show 100× brightfield images of posts after incubation with microbes (top row) and corresponding histogram plots of microbial growth area from post exterior from 200 representative supports (bottom row). FIG. 6A shows the results for Si support with WGA-A488 lectin; FIG. 6B shows the results for Si support with LcH-TRITC lectin; and FIG. 6C shows the results for Si support with BSA. Arrows denote attached microbes. Preferential adhesion to the support edges was also noted here, with significantly higher levels of microbes present on WGA-A488 lectin supports compared to LcH-TRITC lectin or BSA supports ($p<0.01$). However, when comparing the adhered microbe area on WGA-A488 lectin functionalized PGMA-PVDMA supports to WGA-A488 lectin functionalized Si supports (FIGS. 5A and 6A), a statistically significant decrease in microbe area in the Si supports is identified ($p<0.01$).

The data from FIGS. 5A-5C and 6A-6C is further summarized in Table 1, shown below, which quantifies the increase in support area due to microbial adhesion for each capture protein on both PGMA-PVDMA and Si supports. The enhanced levels of lectin-specific microbial adhesion measured when using PGMA-PVDMA as a support give this material promise for further use in lectin-based cellular screening assays.

TABLE 1

Microbe accumulation onto modified PGMA-PVDMA patterned polymer and Si posts after protein functionalization and microbial adhesion

| Capture Protein | Support Material | Support area ($\mu m^2$) | Support area with microbes ($\mu m^2$) | % increase |
|---|---|---|---|---|
| WGA-A488 | PGMA-PVDMA | 92 ± 4 | 153 ± 34 | 66 |
| | Silicon | 93 ± 4 | 114 ± 13 | 23 |
| LcH-TRITC | PGMA-PVDMA | 69 ± 2 | 78 ± 15 | 13 |
| | Silicon | 148 ± 4 | 143 ± 9 | 0 |
| BSA | PGMA-PVDMA | 72 ± 3 | 75 ± 5 | 4 |
| | Silicon | 109 ± 2 | 107 ± 6 | 0 |

Figures 7A, 7B:
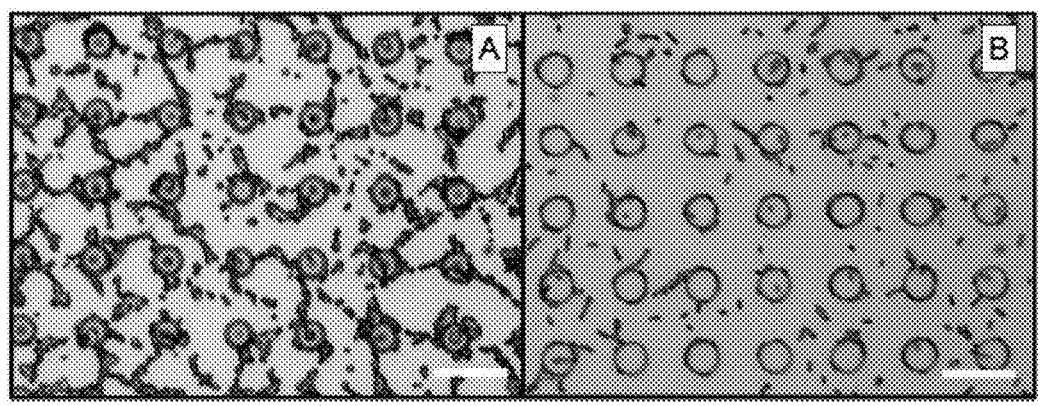
FIGS. 7A, 7B. 50× brightfield images of P. Fluorescens adhesion to (A) WGA lectin-functionalized PGMA-PVDMA supports, and (B) WGA lectin-functionalized Si supports. Scale bar=20 μm.

FIGS. 7A and 7B are 50× brightfield images showing *P. Fluorescens* adhesion to WGA lectin-functionalized PGMA-PVDMA supports (FIG. 7A), and WGA lectin-functionalized Si supports (FIG. 7B). As evidenced by the side-by-side comparison, the WGA lectin-functionalized PGMA-PVDMA support exhibited a significantly improved cell capture density compared to the WGA lectin-functionalized Si supports.

Conclusions

There is an unmet need in cell-based assays for creating surfaces that promote the selective and efficient capture of target cells. Platforms based on lectin-carbohydrate recognition can be used to selectively probe the carbohydrate-rich surface of active microbial cells, but generally lack the high affinities necessary for efficient capture. In this disclosure, the design and fabrication of high-avidity surface supports that combine high concentrations of covalently immobilized lectins with micron-scale surface topography are described for overcoming this challenge. The PGMA-b-PVDMA polymers previously reported for tailoring surface functionality (Lokitz et al., 2012, Ibid.) have herein been modified into patterned and three-dimensional surface supports for lectin modification and subsequent microbe capture. Increased levels of microbe adhesion and colony formation measured on different lectin-functionalized PGMA-b-PVDMA, as compared with silicon supports, demonstrate the positive combined impact of high-lectin concentration and physical structure on microbe capture. Continued refinements of this approach, aimed at understanding the impact of specific three-dimensional geometries on capture efficiency and increasing the variety of lectins used in screening promises, will lead to further enhancements, ultimately leading to an experimental platform that will characterize the dynamics of microbial EPS expression with environmental cues, while also enabling "catch and release" applications aimed at providing enrichment of microbial sub-populations for sequencing.

EXAMPLE 2

Materials

PGMA-b-PVDMA, of GMA and VDMA block lengths of 56 and 178, was synthesized and characterized, as detailed above. All PGMA-b-PVDMA was stored dried at 4° C. until use. Four-inch silicon wafers obtained from Silicon Quest were used as substrates. *Triticum vulgare* lectin (Wheat germ agglutinin, WGA) was re-suspended in 1× phosphate buffered saline (PBS; 137 mM NaCl, 2.7 mM KCl, 10 mM $Na_2HPO_4$, 2 mM $KH_2PO_4$, pH 7.4) to 1 mg/mL, flash frozen with liquid nitrogen, and stored at −80° C. until use. Fluorescent microbe labeling was conducted with FM® 1-43 Dye or SYTO® 85 (Life Technologies). FM® 1-43 Dye was suspended to a concentration of 1 mg/mL in 1× PBS and stored at −80° C. until use. SYTO® 85 was suspended at 5 mM in DMSO and stored at −20° C. until use. Both of these dyes were able to label microbes with high levels of fluorescence intensity. *Pseudomonas fluorescens* GM30 was used as the target microbe and stored in glycerol stocks at −80° C. until use. All other chemicals were used as received.

Lithographic Patterning of PGMA-b-PVDMA Films

Figures 12A, 12B:
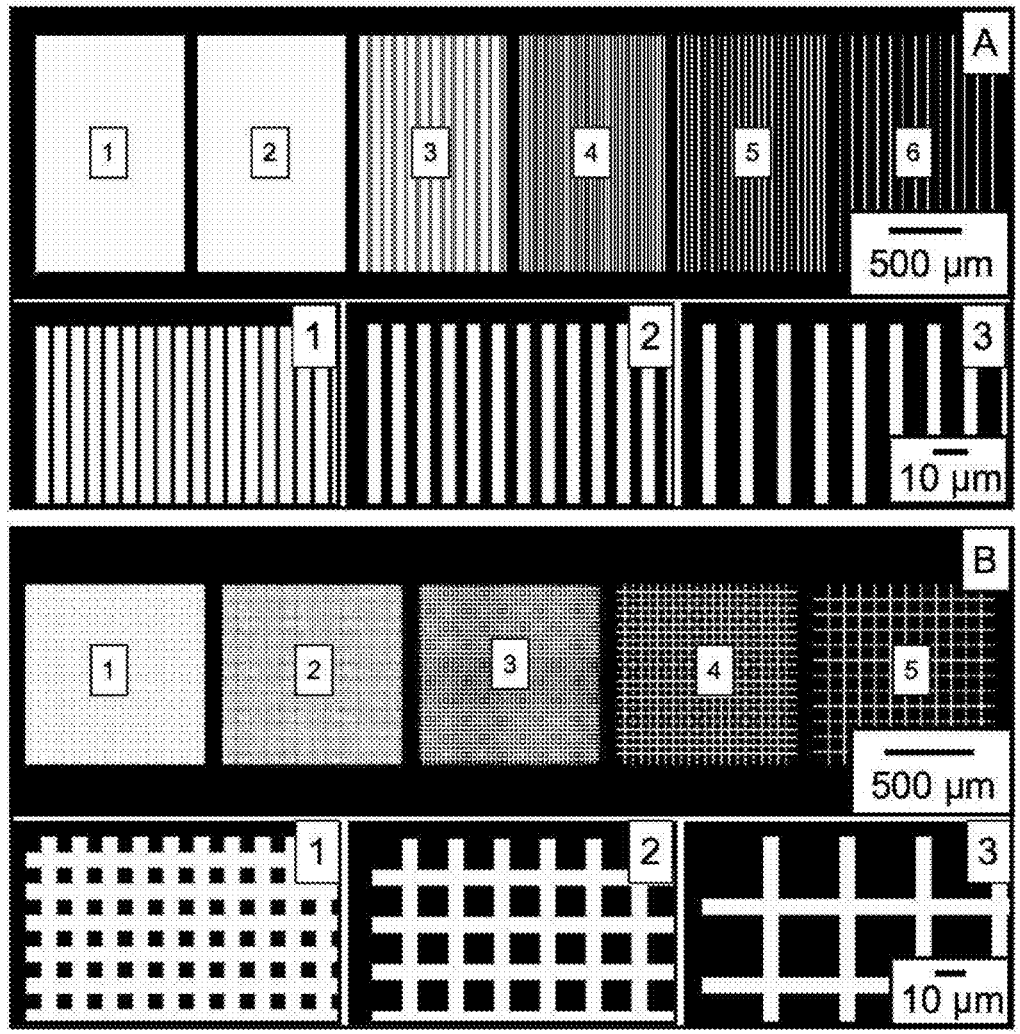
FIGS. 12A, 12B. Layout of a line and grid patterns containing PGMA-b-PVDMA patterned films (white) on silicon substrates (black). A) Top Row (FIG. 12A): Layout of the six line arrays. Line arrays have increased pitch moving from left to right. Bottom Row: Zoomed-in layout of arrays 1, 2, and 3, which contain 5 μm wide lines with a pitch of 7, 10, and 15 μm, respectively. B) Top Row: Layout of the five square grid patterns. Grids have increased pitch moving from left to right. Bottom Row (FIG. 12B): Zoomed-in layout of square grids 1, 2, and 3, which contain 5 μm wide lines with a pitch of 10, 15, and 25 μm, respectively.

Each wafer consisted of nine replicate pattern sets. The layout of a pattern set is described in FIGS. 12A and 12B. Each pattern set consisted of six line arrays and five square grids. Within each line array were 5 μm-wide parallel rectangular strips with constant pitch (line center to line center distance). The six line arrays contained a pitch of 7, 10, 15, 25, 45 and 85 μm. Square grid patterns consisted of 5 μm-wide parallel rectangular strips running perpendicular to a second set of 5 μm-wide parallel rectangular strips. The five square grid patterns had a varied pitch of 10, 15, 25, 45, and 85 μm. The overall area of each line array was 1.6 $mm^2$ and the overall area of each grid was 1.0 $mm^2$ Conventional photolithographic methods were used to first modify the silicon wafers with patterned photoresist, as detailed above. After photoresist patterning, substrates were treated with $O_2$ plasma for 3 minutes, and then replicate pattern sets were diced into 20×20 mm substrates. Each substrate was spin-coated (1500 rpm, 15 s) with 100 μl quantities of a 1 wt % solution of PGMA-b-PVDMA in anhydrous chloroform and annealed for 18 hours at 110° C. Substrates were then sonicated in acetone for 5 minutes to remove the photoresist, leaving behind the patterned PGMA-b-PVDMA films. Substrates were finally rinsed in isopropyl alcohol, dried in $N_2$, and stored in a vacuum desiccator until use.

WGA Functionalization and Microbial Incubation

*P. fluorescens* GM30 was used as a model microbe in this system and WGA lectin was used as a complementary capture protein due to the high levels of association. WGA was incubated over the patterned surfaces at 1 mg/mL for 1 hour. As a negative control to test for nonspecific interactions between microbes and the patterned substrate, surfaces were also functionalized with BSA at the same conditions. *P. fluorescens* was cultured on LB Agar plates at 29° C. for 24-48 hrs and stored at 4° C. for up to one week. Liquid cultures were grown by inoculating 5 mL of LB media with a single colony and growing at 29° C. with shaking to the logarithmic phase. The cells were then harvested by centrifugation, washed in 1× PBS, and re-suspended in 1× PBS at an $OD_{600}$ of 1.0. FM® 1-43 or SYTO® 85 dye was then added to the washed microbes at a concentration of 1 µg/mL, incubated for 1 hour, and then washed with 1× PBS to remove unbound dye. Microbes were finally diluted to a final concentration of $OD_{600}$=0.1 in 1× PBS and incubated over the WGA-functionalized substrates for 1 hour. The substrates were then washed to remove unbound cells, and the adherent cells fixed with a 2.5% glutaraldehyde solution in $H_2O$ and then dried via aspiration. Microbial adhesion to WGA-functionalized substrates was tested in triplicate.

Analysis

Brightfield and fluorescence microscopy. All brightfield and fluorescence images (20×, NA 0.4/100×, NA 0.95) were taken with an upright microscope (BX51, Olympus) using a 16-bit CCD camera (Luminera Corporation, Ottowa, ON) and Infinity Capture software. All fluorescence images (green filter set) were taken either at 20× magnification (4×4 binning, 0.5 s exposure time, 1.5 gain) or at 100× magnification (4×4 binning, 0.5 s exposure time, 1.0 gain). Fluorescent images showing the captured microbes were used for quantitative image analysis. Brightfield images of the microbes and PGMA-b-PVDMA films were for visualization only and not used in image analysis.

Atomic force microscopy (AFM). All AFM images were taken using a Park Systems AFM operating in contact mode with NanoWorld PNP-TR B cantilevers (17 kHz, 0.08 $Nm^{-1}$). Patterned regions were imaged at 90×90 µm, 20×20 µm and 10×10 µm areas. PGMA-b-PVDMA film thickness, maximum edge height, and average roughness ($R_a$) were analyzed using XEI Park System software. $R_a$ measurements were measured from a 2×2 µm region of interest centered directly over the edge region or over the internal PGMA-b-PVDMA pattern regions (regions of maximum distance from the edges). Three replicate substrates were analyzed in all measurements.

Scanning electron microscopy (SEM). A Carl Zeiss Merlin SEM was used to image patterned PGMA-b-PVDMA films. Charge compensation was used during sample imaging and no sample pretreatment was required. The SEM was operated at 1.7 kV and all images were taken at 5-6.5 K× magnification.

Figures 13A, 13B, 13C, 13D, 13E, 13F, 13G, 13H:
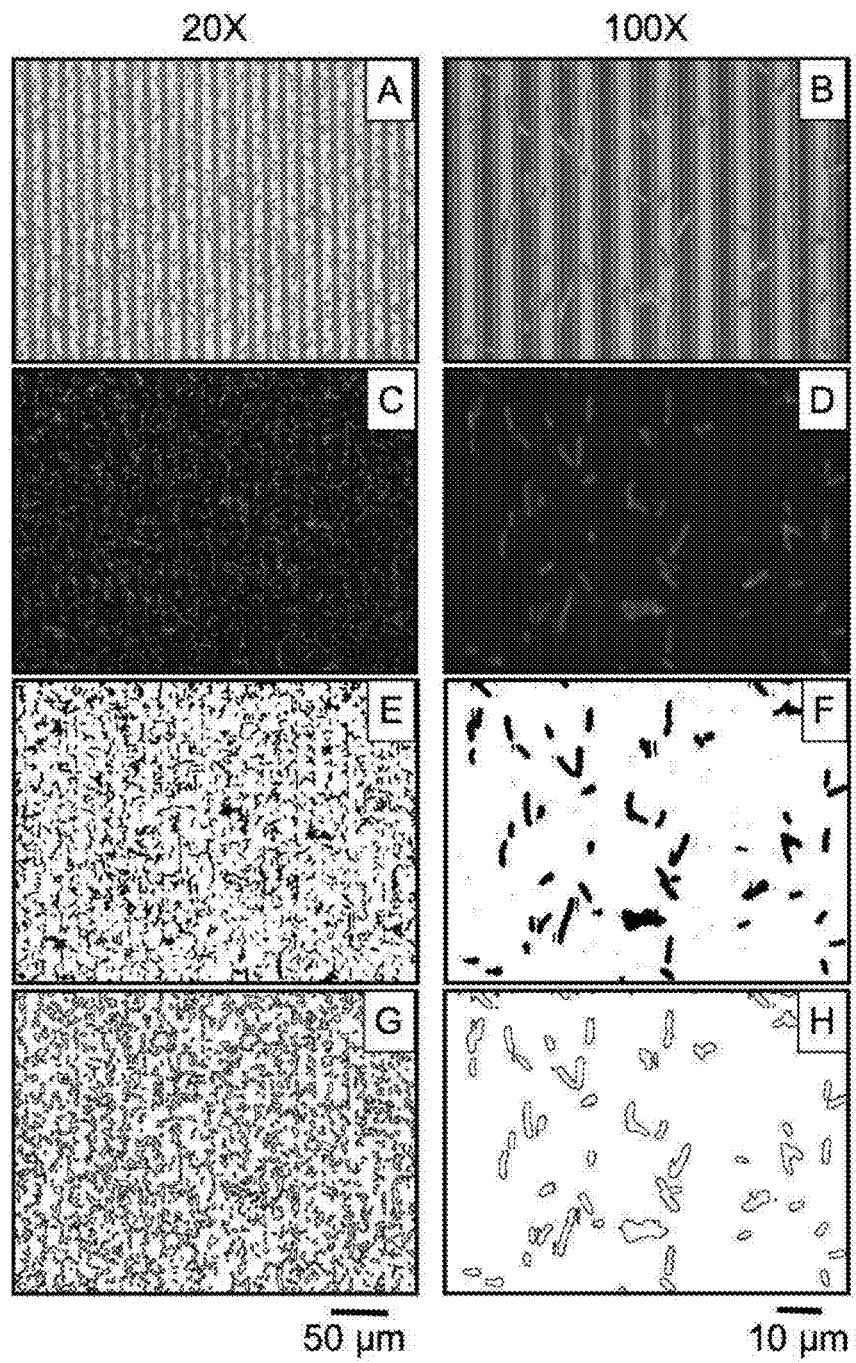
FIGS. 13A-13H. Image processing of microbial aggregates on surfaces containing patterned PGMA-b-PVDMA films. A) and B) 20× and 100× composite brightfield-fluorescence images of P. fluorescens microbe captured onto WGA-functionalized PGMA-b-PVDMA line arrays. C) and D) Fluorescence images of microbes only. E) and F) Binary images of microbes after image processing. G) and H) Particle outlines for measurement of aggregate size and distribution.

Image processing and data analysis. Two-dimensional measurements of microbe aggregate area were determined using image thresholding and particle analysis with the Triangle method (ImageJ 1.47 v). An example of the image processing method is shown in FIGS. 13A-13H. FIGS. 13A and 13B display two example composite brightfield-fluorescence images at 20× and 100× magnification, respectively, which show the position of the fluorescent microbes in relation to the non-fluorescence polymer pattern. These images were used only to visualize the placement of microbes relative to the polymer pattern. FIGS. 13C and 13D show the raw fluorescence images from FIGS. 13A and 13B, respectively. The raw fluorescent images were processed with ImageJ image thresholding into binary images such as those shown in FIGS. 13E and 13F. Finally, ImageJ particle analysis was performed on the binary images to provide outlines of the microbe aggregates, such as those shown in FIGS. 13G and 13H, and to generate the aggregate area data in FIGS. 9, 10, and 11. Three representative 20× fluorescent images per pattern were analyzed on each substrate. Three replicate substrates were measured. Microbes both attached to the PGMA-b-PVDMA films and attached onto the silicon regions were included in the measurement. Histogram plots with a bin size of 10 $\mu m^2$ were generated from this data, and all aggregates with areas >300 $\mu m^2$ were combined into one bin.

Results and Discussion

Characterization of PGMA-b-PVDMA Films of Varied Shapes and Dimensions

Figures 8A, 8B, 8C, 8D, 8E, 8F:
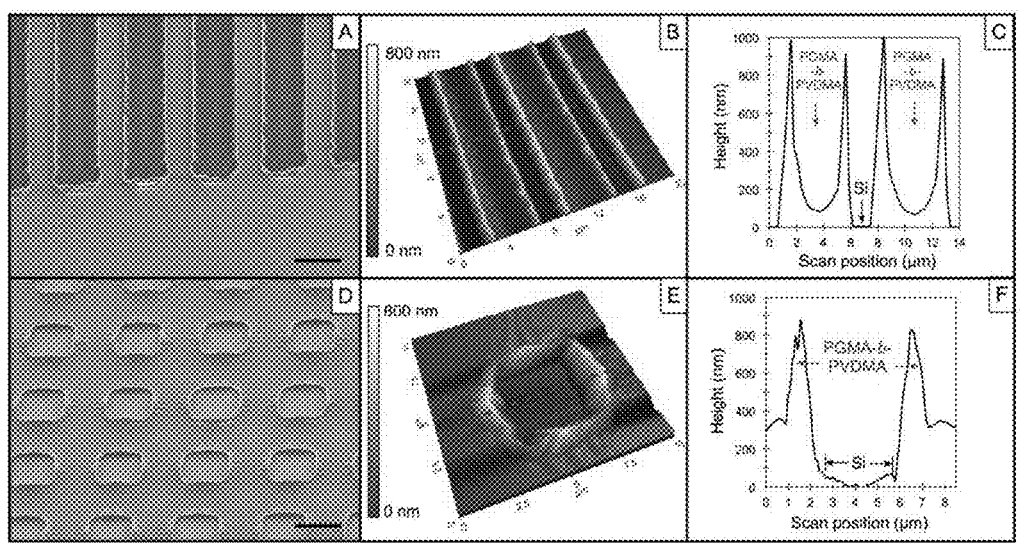
FIGS. 8A-8F. Characterization of PGMA-b-PVDMA patterned films. (A) SEM and (B) AFM contact mode image of films patterned as 5 μm wide line arrays with a 7 μm pitch. (C) Cross-sectional height profile of dashed line in B. (D) SEM image and (E) AFM contact mode image of films patterned as square grids with a 10 μm pitch. (F) Cross-sectional height profile of dashed line in E.

The formation of patterned PGMA-b-PVDMA films was achieved through lithographic patterning followed by spin-coating, annealing at 110° C., and wet liftoff to remove photoresist. The annealing step permitted surface attachment to occur between GMA epoxy groups and surface hydroxyl groups and also for the crosslinking of GMA groups throughout the polymer, resulting in mechanically stable films. FIGS. 8A and 8B show SEM and AFM images, respectively, of films patterned as 5 µm wide line arrays with a 7 µm pitch. As shown in the height profiles of FIG. 8C, these films have a non-uniform cross-sectional thickness with a maximum thickness of 930±32 nm occurring at the film edges. This is due to the fact that the polymer covers the ~1 µm high photoresist edges during the spin coating step. A minimal film thickness of 110±20 nm occurs near the center of the film cross section. This thickness approaches the brush length for this copolymer.

The SEM image, AFM image, and height profile of films patterned as square grids with a 10 µm pitch are shown in FIGS. 8D-8F, respectively. As shown, the square grid arrays exhibit a similar surface topology compared to the line arrays. A maximum thickness of 860±80 nm was found at the film edges, and a minimal film thickness of 360±73 nm was measured. For line array and grid films, the average surface roughness ($R_a$) from the interior PGMA-b-PVDMA pattern region was 12±2 nm and 9±4 nm, respectively. In contrast, the outer edge regions of the films contain pronounced surface topography and higher average surface roughness ($R_a$~180 nm for both patterns). These outer-edge features have been shown to be most favorable for the capture of microbes after lectin functionalization. The thick, pronounced edge features also serve as physical barriers that separate PGMA-b-PVDMA regions from flat silicon regions to form a spatially confined surface environment at the length scale of a microbe (~1-5 µm).

Microbial Adhesion on WGA-functionalized PGMA-b-PVDMA Line Arrays

To investigate the capture of *P. fluorescens* microbes over the linear PGMA-b-PVDMA patterned films, substrates were first functionalized with WGA capture lectins. WGA covalently couples to the films through addition of lysine residues onto pendant VDMA groups and also adsorbs onto silicon regions of the surface. After incubation with *P. fluorescens*, the microbes were captured in each of the patterned regions as shown in the 100× brightfield fluorescence images in FIGS. 9A-9E, which correspond to line arrays with a pitch of 7 µm, 10 µM, 15 µM, 25 µm, and 45 µm, respectively. In contrast, control substrates containing identical patterns but that were functionalized with BSA showed no significant levels of microbe adhesion, which is consistent with previous reports and verifies affinity-based capture using WGA as opposed to non-specific surface adhesion and colonization.

Figures 9A, 9B, 9C, 9D, 9E:
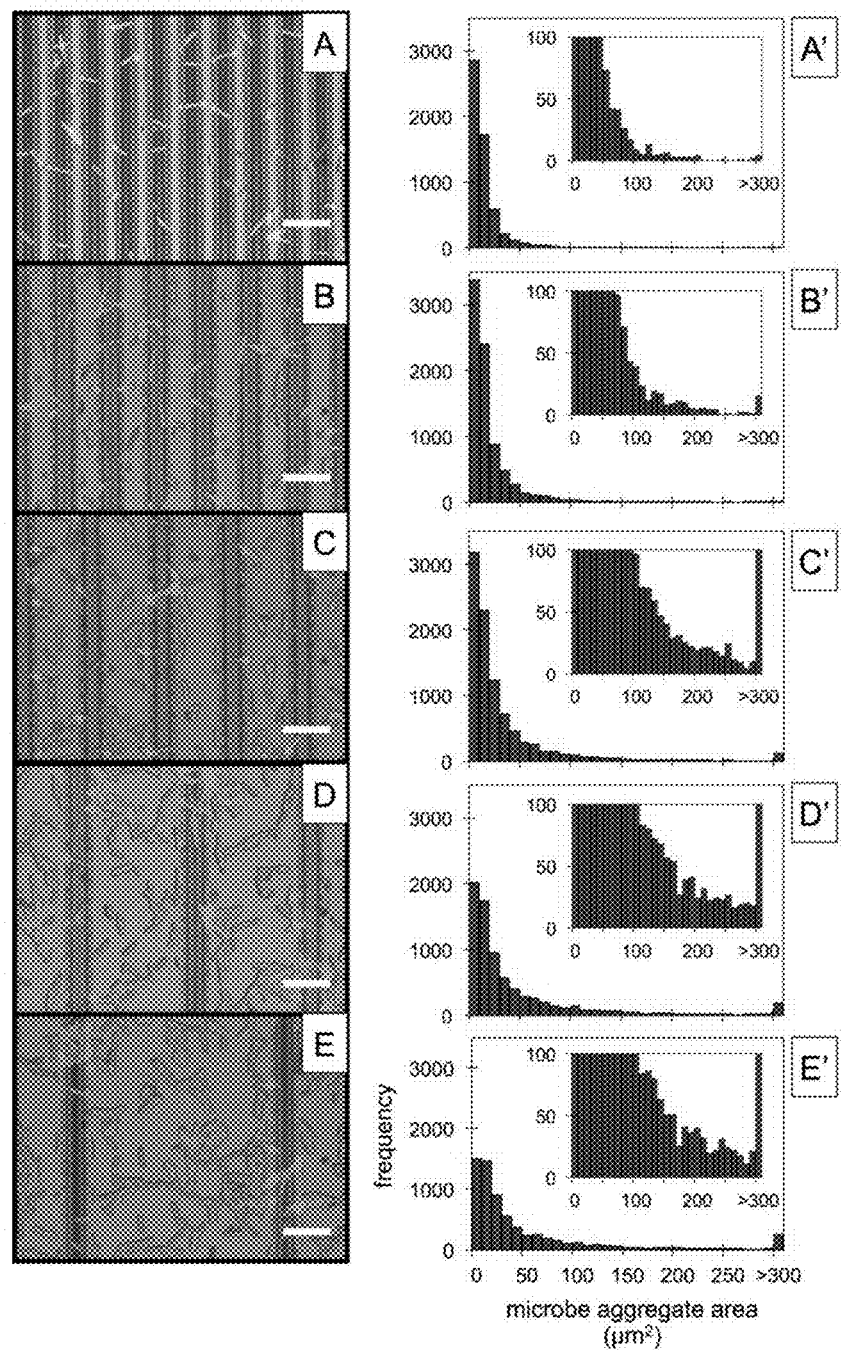
FIGS. 9A-9E and 9A'-9E'. Adhesion of P. fluorescens to PGMA-b-PVDMA line arrays. Left column (FIGS. 9A-9E): Brightfield—fluorescence images (100×) of surfaces containing PGMA-b-PVDMA films patterned as line arrays with a pitch of (A) 7 μm, (B) 10 μm, (C) 15 μm, (D) 25 μm, and (E) 45 μm after WGA functionalization and microbe incubation (scale bar=10 μm). Right column (FIGS. 9A'-9E'): Corresponding histogram plots of aggregate sizes measured over a 2.0 mm² area for each line array and zoomed-in histogram plots (inset) showing the frequencies of larger aggregates.
Figures 10A, 10B, 10C, 10D, 10E:
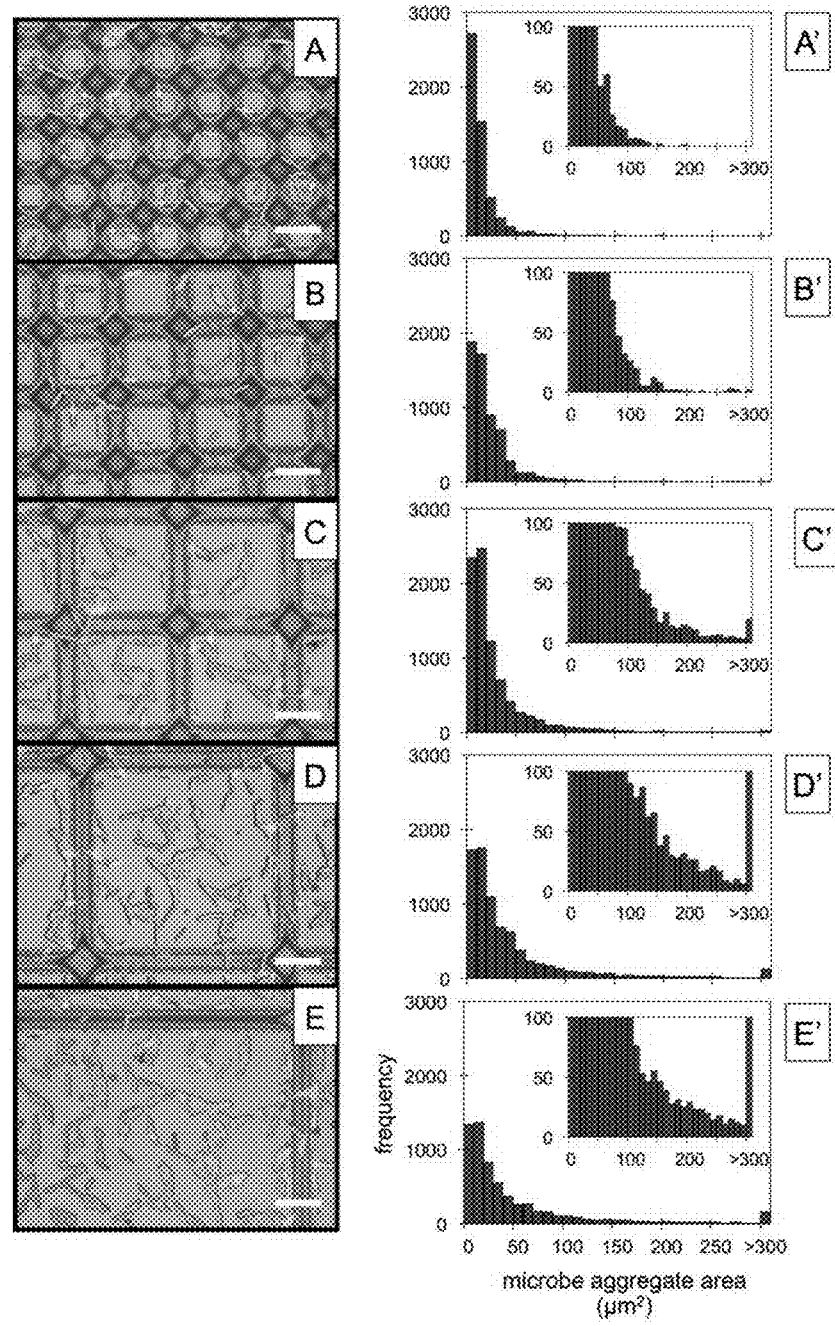
FIGS. 10A-10E and 10A'-10E'. Adhesion of P. fluorescens to PGMA-b-PVDMA grids. Left column (FIGS. 10A-10E): Brightfield—fluorescence images (100×) of surfaces containing PGMA-b-PVDMA films patterned as square grids with a pitch of (A) 10 μm, (B) 15 μm, (C) 25 μm, (D) 45 μm, and (E) 85 μm after WGA-functionalization and microbe incubation (scale bar=10 μm). Right column (FIGS. 10A'-10E'): Corresponding histogram plots of aggregate sizes measured over a 2.0 mm² area for each grid and zoomed-in histogram plots (inset) showing the frequencies of larger aggregates.

A comparison of the corresponding histogram plots in FIGS. 9A'-9E' shows that there is a difference in the microbial aggregate size distribution, which depends on the degree of spatial confinement present within the line patterns. Microbes present over the lines with the smallest pitch in FIG. 9A exist predominantly as single or paired cells. This is reflected by the histogram data in FIG. 9A', showing that 79% of microbes analyzed during image analysis had less than a 20 µm$^2$ particle area while only 1% existed as large aggregates with areas greater than 100 µm$^2$. Here, microbes appear bound across the tops and on the sides of the films. However, capture is limited by restricted access to the outer-edge regions of the films, where the pronounced microscale surface topography and high surface roughness are most favorable for capture. Additionally, the topology depicted in FIG. 8A causes micron-scale surface confinement that restricts the interactions between surface-associated microbes, which limits the formation of aggregates. As the line pitch increases to 10, 15, and 25 µm, incrementally larger aggregates appear on the surface, which causes incremental increases in size distribution, as shown in FIGS. 9B'-9D'. The increase is due to less confined access to the outer edges of the films as well as to the flat silicon-WGA regions of the surface that promote interaction between surface-associated microbes. A minor effect is noted over the last spacing step (25 to 45 µm line pitch, FIGS. 9D and 9E), where microbe capture is dominated by the flat silicon-WGA surfaces with little influence from the PGMA-b-PVDMA line patterns.

These results suggest that the size of captured aggregates can be tuned based on the surface topological features and underscore the importance of highly confined features (<10 µm) for limiting microbial aggregation during capture. Similar trends with *P. fluorescens* have been reported from Diaz, et. al. (Diaz, C., et. al., *Langmuir*, 2007, 23, pp. 11206-11210; and Diaz, C., et. al., *ACS Appl. Mater. Interfaces*, 2009, 1, pp. 136-143.), where sub-micron lines were etched into silicon surfaces and found to restrict adhesion, aggregation, and cell motility on the surface. The ability to inhibit aggregation during microbe capture is particularly useful for assays that implement affinity-based catch-and-release of microbes for secondary genomic or proteomic analysis, which may require individual cellular isolates. For example, single cell isolation would be important to avoid changes in gene or protein expression arising from the presence of extracellular quorum sensing molecules, such as acyl-homoserine lactone, which are produced at dramatically higher levels in dense populations of Gram-negative bacteria.

Microbial Adhesion onto WGA-Functionalized PGMA-b-PVDMA Grids

In an effort to further control the size distribution of captured microbes, a second dimension of spatial confinement was introduced to the patterns by formation of square grids. Similar to the line arrays, the grid pitch was systematically varied at 10, 15, 25, 45, and 85 µm. Upon WGA functionalization and incubation of *P. fluorescens*, surface-associated microbes became bound to the grids, as shown in the brightfield fluorescence images of FIGS. 10A-10E, which display representative 100× images of grid patterns having a pitch of 10, 15, 25, 45, and 85 µm, respectively. The respective aggregate size distributions are provided in FIGS. 10A'-10E'. As with the line arrays, aggregate size distribution was dependent on pitch, as patterns with smaller pitch, and thus, higher levels of confinement, reduced the formation of larger aggregates. In the case of the square grids with a 10 µm pitch, 80% of microbes appear as individual or pair-wise aggregates, while only 0.45% of particles had areas greater than 100 µm$^2$.

Figure 11:
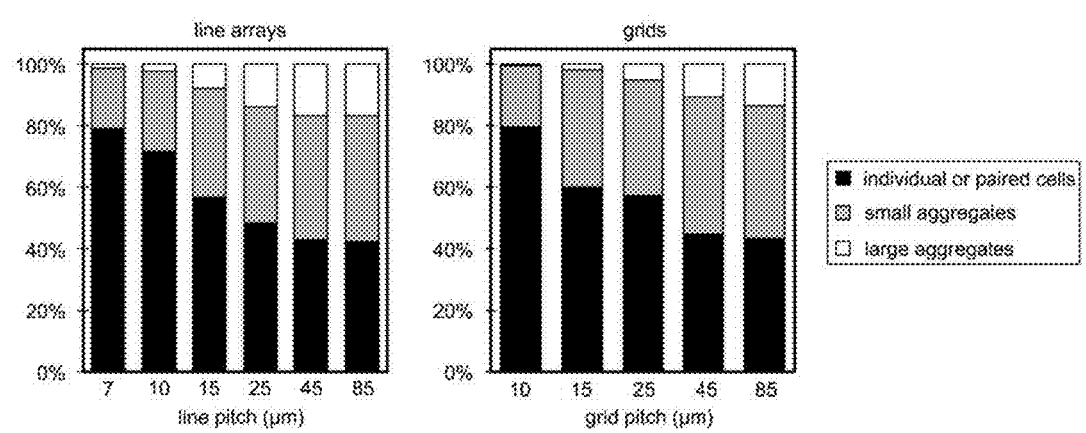
FIG. 11. Percentage of microbes existing as individual or paired cells (<20 μm²), small aggregates (20-100 μm²), and large aggregates (>100 μm²) after capture and image analysis for each pitch on PGMA-b-PVDMA line arrays (left) and grids (right).

FIG. 11 presents a direct comparison of aggregate size distributions measured between line and grid patterns. Here, captured microbes were binned into three size categories: i) individual or paired cells (<20 µm$^2$); ii) small aggregates (20-100 µm$^2$); and iii) large aggregates (>100 µm$^2$), and the percentage of microbes falling within each size category is displayed. For the line arrays (FIG. 11, left), it is apparent that the fraction of large aggregates increases while the fraction of individual or paired cells decreases with increased pitch up to 45 µm. Grid patterns (FIG. 11, right) show similar trends; however, the percentage of large aggregates formed over the grids is smaller compared to line arrays of the same pitch. Additionally, the influence of the PGMA-b-PVDMA film on aggregate size distribution is apparent within grids with a pitch up to 85 µm. These differences are likely due to the additional dimension of spatial confinement introduced by the grids, and suggest that grid geometries are preferable for the lectin-based capture of individual microbes.

Conclusions

Surfaces have herein been developed that contain microstructured, bioactive surface polymers with varied degrees of spatial confinement to control the size of microbial aggregates captured through a functional binding event. While other approaches have emphasized control of microbial surface colonization by physical structures, described in this disclosure is the novel combination of physical confinement and affinity-based capture. These substrates can be used for flow-based catch-and-release assays that functionally isolate microbe sub-populations based on EPS content while avoiding biofilm or aggregate formation on the capture surface. As a secondary utility, these surfaces should also provide a useful platform for investigating symbiotic or pathogenic relationships between isolated microbe populations of controlled sizes, ranging from pair-wise interactions to interactions within large populations, which can improve current knowledge pertaining to cell signaling and its relation to population size.

While there have been shown and described what are at present considered the preferred embodiments of the invention, those skilled in the art may make various changes and modifications which remain within the scope of the invention defined by the appended claims.

What is claimed is:

1. A composition useful for cell capture, the composition comprising a solid substrate on which is covalently affixed a patterned polymer having a substantially planar surface defined by x- and y-axes perpendicular to each other, and an array of regularly spaced protruded shapes on said substantially planar surface, wherein said array of regularly spaced protruded shapes has a set frequency of occurrence and a pattern density, each protruded shape being vertically raised along a z-axis perpendicular to the x- and y-axes of the substantially planar surface; having a height along the z-axis of at least 100 nm; and possessing an outer perimeter along the x- and y-axes, wherein said outer perimeter along the x- and y-axes for each protruded shape is vertically raised along the z-axis by a greater extent than portions of the z-axis of the protruded shape within the confines of the outer perimeter along the x- and y-axes, and cell-targeting agents covalently attached to said patterned polymer by a cross-linking group, wherein said cell-targeting agents are lectin and are exposed.

2. The composition of claim 1, wherein said cell-targeting agent is a microbe-targeting agent.

3. The composition of claim 1, wherein said patterned polymer is a block-copolymer.

4. The composition of claim 1, wherein said patterned polymer is a vinyl addition polymer.

5. The composition of claim 1, wherein said solid substrate is selected from the group consisting of metal, metal oxide, semiconductor, and plastic.

6. A method of capturing cells, the method comprising contacting a cell capturing composition with said cells, the cell-capturing composition comprising the composition of claim 1.

7. The method of claim 6, wherein said cell-targeting agent is a microbe-targeting agent.

8. The method of claim 6, wherein said patterned polymer is a block-copolymer.

9. The method of claim 6, wherein said patterned polymer is a vinyl addition polymer.

10. The method of claim 6, wherein said solid substrate is selected from the group consisting of metal, metal oxide, semiconductor, and plastic.

11. The method of claim 6, wherein said cells are microbes.

12. The method of claim 6, wherein said cell-targeting agent is selective for a cell type.

13. The method of claim 6, wherein said cell-targeting agent is selective for a genus or species of a microbe.

14. The method of claim 6, wherein said cell-capturing composition is incorporated in a flow-through device.

15. The method of claim 6, wherein said cells are within a liquid.

16. The method of claim 6, wherein said cells are in air.

17. The composition of claim 1, wherein said crosslinking group is a ring-opened azlactone group.

18. The composition of claim 1, wherein each protruded shape has a height of at least 500 nm.

19. The composition of claim 1, wherein said protruded shapes are selected from the group consisting of linear, circular, and polygonal protruded shapes.

* * * * *